US009962367B2

(12) United States Patent
Chollet et al.

(10) Patent No.: US 9,962,367 B2
(45) Date of Patent: *May 8, 2018

(54) ORAL FORMULATIONS OF PYRROLIDINE DERIVATIVES

(71) Applicant: ObsEva S.A., Plan-les-Ouates (CH)

(72) Inventors: Andre Chollet, Plan-les-Ouates (CH); Oliver Pohl, Plan-les-Ouates (CH)

(73) Assignee: Obseva S.A., Plan-Les-Ouates (CH)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/571,615

(22) Filed: Dec. 16, 2014

(65) Prior Publication Data

US 2015/0164859 A1  Jun. 18, 2015

(30) Foreign Application Priority Data

Dec. 17, 2013 (EP) ..................................... 13197606

(51) Int. Cl.
| | | |
|---|---|---|
| *A61K 31/09* | (2006.01) | |
| *A61K 9/14* | (2006.01) | |
| *A61P 29/00* | (2006.01) | |
| *A61P 35/00* | (2006.01) | |
| *B82Y 5/00* | (2011.01) | |
| *A61K 31/40* | (2006.01) | |
| *A61K 31/401* | (2006.01) | |
| *A61K 9/20* | (2006.01) | |
| *A61K 9/00* | (2006.01) | |
| *A61K 47/40* | (2006.01) | |
| *A61K 45/06* | (2006.01) | |

(52) U.S. Cl.
CPC ............ *A61K 31/40* (2013.01); *A61K 9/0056* (2013.01); *A61K 9/0095* (2013.01); *A61K 9/20* (2013.01); *A61K 9/2009* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 31/401* (2013.01); *A61K 45/06* (2013.01); *A61K 47/40* (2013.01)

(58) Field of Classification Search
None
See application file for complete search history.

(56) References Cited

U.S. PATENT DOCUMENTS

| | | | | |
|---|---|---|---|---|
| 5,047,247 | A * | 9/1991 | Milovac et al. | ............... 424/465 |
| 5,069,910 | A * | 12/1991 | Kovacic | ............... A61K 9/2004 |
| | | | | 424/456 |
| 6,329,418 | B1 | 12/2001 | Cheng et al. | |
| 7,115,639 | B2 | 10/2006 | Schwarz et al. | |
| 7,115,754 | B2 | 10/2006 | Jorand-Lebrun et al. | |
| 7,189,754 | B2 | 3/2007 | Schwarz et al. | |
| 7,211,601 | B2 * | 5/2007 | Halazy | ................. C07D 207/22 |
| | | | | 514/423 |
| 9,670,155 | B2 | 6/2017 | Chollet | |
| 2003/0105030 | A1 * | 6/2003 | Liao et al. | ........................ 514/27 |
| 2003/0180352 | A1 * | 9/2003 | Patel et al. | ..................... 424/465 |
| 2004/0147511 | A1 | 7/2004 | Schwarz et al. | |
| 2004/0220238 | A1 | 11/2004 | Schwarz et al. | |
| 2006/0004020 | A1 * | 1/2006 | Jorand-Lebrun et al. | ........................ 514/254.01 |
| 2007/0037806 | A1 | 2/2007 | Schwarz et al. | |
| 2007/0129381 | A1 | 6/2007 | Schwarz et al. | |
| 2007/0197794 | A1 | 8/2007 | Nadler et al. | |
| 2008/0038342 | A1 * | 2/2008 | Bergman et al. | ............. 424/465 |
| 2015/0073032 | A1 | 3/2015 | Chollet | |
| 2015/0164859 | A1 | 6/2015 | Chollet et al. | |
| 2016/0221944 | A1 | 4/2016 | Chollet | |
| 2016/0002160 | A1 | 7/2016 | Chollet | |
| 2017/0065556 | A1 | 3/2017 | Chollet et al. | |

FOREIGN PATENT DOCUMENTS

| | | |
|---|---|---|
| CN | 1678576 A | 10/2005 |
| EP | 2845850 A1 | 3/2015 |
| EP | 2845850 A1 | 3/2015 |
| EP | 2886107 A1 | 6/2015 |
| JP | 2004-534804 A | 11/2004 |
| JP | 2005-533828 A | 11/2005 |
| WO | WO-99/52868 A1 | 10/1999 |
| WO | 02/074741 A1 | 9/2002 |
| WO | WO-02/074741 A1 | 9/2002 |
| WO | WO-02/102799 A2 | 12/2002 |
| WO | 2004/005249 A1 | 1/2004 |
| WO | WO-2004/005249 A1 | 1/2004 |
| WO | 2004/076407 A2 | 9/2004 |
| WO | WO-2004/076407 A2 | 9/2004 |
| WO | 2005/082848 A2 | 9/2005 |

(Continued)

OTHER PUBLICATIONS

Surfactant Definition at www.britannica.com/science/surfactant (retrieved from the internet Dec. 2, 2015).*
Polaxamer 188 MSDS at www.sciencelab.com/msds.php?msdsld=9926611 (retrieved from the internet Mar. 25, 2016).*
Guidance For Industry, Drug Metabolism/Drug Interaction Studies in the Drug Development Process: Studies in Vitro, 1997.*
European Search Report issued in European Application No. 13183723.9, dated Oct. 22, 2013 (3 pages).
Decision of Rejection for Japanese Patent Application No. 2016-535134, dated Dec. 6, 2016 (10 pages).
First Office Action for Chinese Patent Application No. 2014800499272, dated Sep. 26, 2016 (8 pages).

(Continued)

*Primary Examiner* — Dennis Heyer
(74) *Attorney, Agent, or Firm* — Clark & Elbing LLP

(57) ABSTRACT

The present invention relates to solid oral formulations comprising a compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, and the use of said formulations in the treatment and/or prevention of preterm labor, premature birth, dysmenorrhea and embryo implantation failure due to uterine contractions. The present invention is furthermore related to processes for their preparation.

3 Claims, 3 Drawing Sheets

(56) References Cited

FOREIGN PATENT DOCUMENTS

WO WO-2005/082848 A2 9/2005

OTHER PUBLICATIONS

International Preliminary Report on Patentability for International Application No. PCT/EP2014/066075, dated Sep. 7, 2015 (5 pages).
Notice of Reasons for Rejection for Japanese Patent Application No. 2016-535134, dated Aug. 2, 2016 (7 pages).
Office Action for Canadian Patent Application No. 2,921,580, dated May 25, 2016 (4 pages).
Office Action for Israeli Patent Application No. 244152, dated May 23, 2016 (3 pages).
Office Action for Korean Patent Application No. 10-2016-7009235, dated Aug. 23, 2016 (9 pages).
Written Opinion for International Patent Application No. PCT/EP2014/066075, dated Aug. 20, 2014 (4 pages).
Written Opinion for Singaporean Application No. 11201601743R, dated Oct. 10, 2016 (5 pages).
Office Action for Eurasian Patent Application No. 201690480/28, received Jan. 31, 2017 (9 pages).
International Search Report issued in corresponding International Application No. PCT/EP2014/066075, dated Aug. 20, 2014 (3 pages).
Guideline for Trials, Bioequivalence to Generic Drugs, Feb. 29, 2012, Pharmaceutical Safety and Environmental Health bureau, Ministry of Health, Labor and Welfare, PFXB/ELD Notification No. 0229.10, Appendix 1.
Q & A, Guideline for Trials, Bioequivalence to Generic Drugs, Feb. 29, 2012, Pharmaceutical Safety and Environmental Health bureau, Ministry of Health, Labor and Welfare, Office Notification Appendix 1.
Basic Operation I, New Experimental Chemistry Lecture 1, Incorporated Chemical Society of Japan Part, Jun. 10, 1985, Ver. 6, p. 341 to p. 351.
Basis of Experiment/Information, Basic Part I, Experimental Chemistry Lecture 1, Incorporated Chemical Society of Japan Part, Ver. 5, Sep. 25, 2003, p. 208 to p. 211.
Organic Polymer Biochemistry, Basic Part IV, Experimental Chemistry Lecture 4, Incorporated Chemical Society of Japan Part, Ver. 5, Sep. 25, 2003, p. 95 to p. 108.
Notice of Reasons for Rejection for Japanese Patent Application No. 2016-535134, dated May 30, 2017 (71 pages).
Mazzanti et al., "Rotation in Biphenyls with a Single Ortho-Substituent", J. Org. Chem. 71:5474-81 (2006).
Lynch et. al., "The Effect of Cytochrome P450 Metabolism on Drug Response, Interactions, and Adverse Effects," Am Fam Physician. 76:391-396 (2007).
Blockeel, C., et al., "Effects of Barusiban and Atosiban on Frequency of Uterine Contractions in the Luteal Phase after Stimulation: A Randomised Placebo-Controlled Trial," (2009).
Fanchin, Renato, et al., "Uterine Contractions at the Time of Embryo Transfer Alter Pregnancy Rates after In-Vitro Fertilization," vol. 13, No. 7, pp. 1968-1974 (1998).
IsHak, Waguih William, et al., "Male Anorgasmia Treated with Oxytocin," J. Sex Med., pp. 1022-1024 (2008).
Moraloglu, Ozlem, et al., "Treatment with Oxytocin Antagonists before Embryo Transfer May Increase Implantation Rates after IVF," vol. 21, pp. 338-343 (2010).
Pierzynski, Piotr, Oxytocin and Vasopressin V1A Receptors as New Therapeutic Targets in Assisted Reproduction, vol. 22, pp. 9-16 (2011).
Murphy, Michael R., et al., "Changes in Oxytocin and Vasopressin Secretion During Sexual Activity in Men," Journal of Clinical Endocrinology and Metabolism, vol. 65, No. 4, pp. 738-741 (1987).
Visnova, H., et al. Effects of Barusiban, A Selective Oxytocin Antagonist, on Uterine Contractility in the Luteal Phase After Controlled Ovarian Stimulation, pp. 242 (2012).
Clement, P., et al., "Brain Oxytocin Receptors Mediate Ejaculation Elicited by 7-hydroxy-2-(di-N-propylamino) tetralin (7-OH-DPAT) in Anaesthetized Rats," British Journal of Pharmacology, pp. 1150-1159 (2008).
Shinghal, Rajesh MD., et al., "Safety and Efficacy of Epelsiban in the Treatment of Men with Premature Ejaculation: A Randomized, Double-Blind, Placebo-Controlled, Fixed-Dose Study," J Sex Med, pp. 1-12 (2013).
Assinder, S.J., "Oxytocin Increases 5α-Reductase Activity of Human Prostate Epithelial Cells, But Not Stromal Cells," The Prostate 68, pp. 115-121 (2008).
Nicholson, Helen D., "Oxytocin:A Paracrine Regulator of Prostatic Function," Reviews of Reproduction 1, pp. 69-72, (1996).
Saniger, Marcela Arrazola, et al., "Alpha-1-Adrenergic Receptor Blockade Modifies Insulin-Regulated Aminopeptidase (IRAP) Activity in Rat Prostate and Modulates Oxytocin Functions," Drug Metabolism Letters, vol. 5, No. 3, pp. 1-5 (2011).
Assinder, S.J., et al., "Effects of Steroids on Oxytocin Secretion by the Human Prostate in vitro," International Journal of Andrology, No. 27, pp. 12-18 (2004).
Farina-Lipari, E., et al., "Presence of Atrial Natriuretic Factor in Normal and Hyperplastic Human Prostate and its relationship with Oxytocin Localisation," European Journal of Histochemistry, vol. 47, Issue 2, pp. 133-138, (2003).
European Search Report issued in European Application No. 13197606.0, dated Mar. 12, 2014 (6 pages).
International Preliminary Report on Patentability issued in International Application No. PCT/EP2014/066075, dated Sep. 7, 2015 (6 pages).
Autism Fact Sheet, NINDS, retrieved from the Internet on Jul. 13, 2015 (URL:http://www.ninds.nih.gov/disorders/autism/detail_autism.htm).
Reply to Written Opinion for International Application PCT/EP2014/066075, dated Apr. 20, 2015 and Annex A (7 pages).
Chollet et al., U.S. Appl. No. 15/104,683, filed Jun. 15, 2016.

* cited by examiner

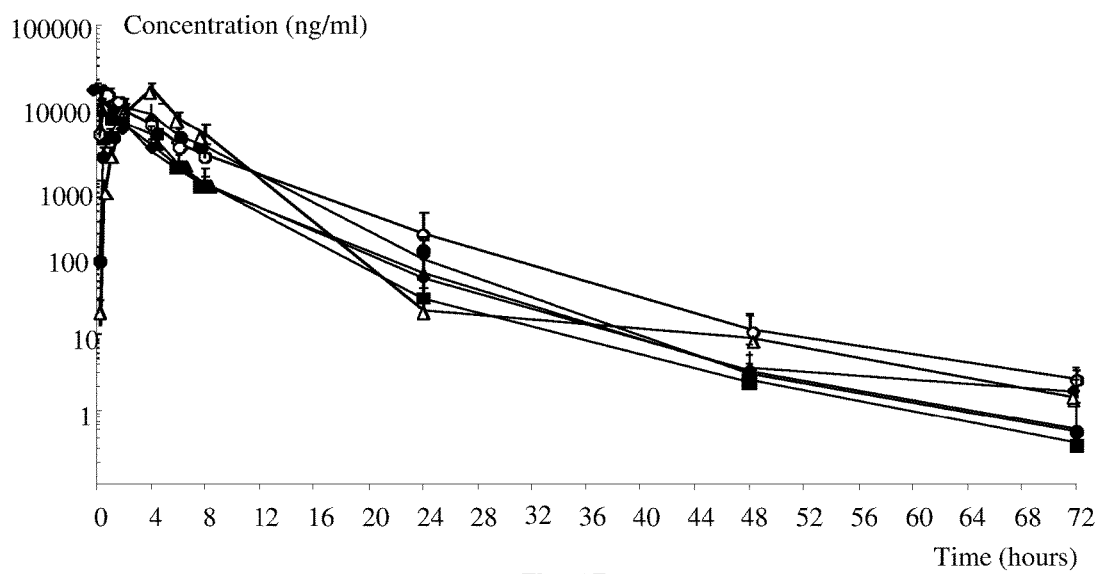
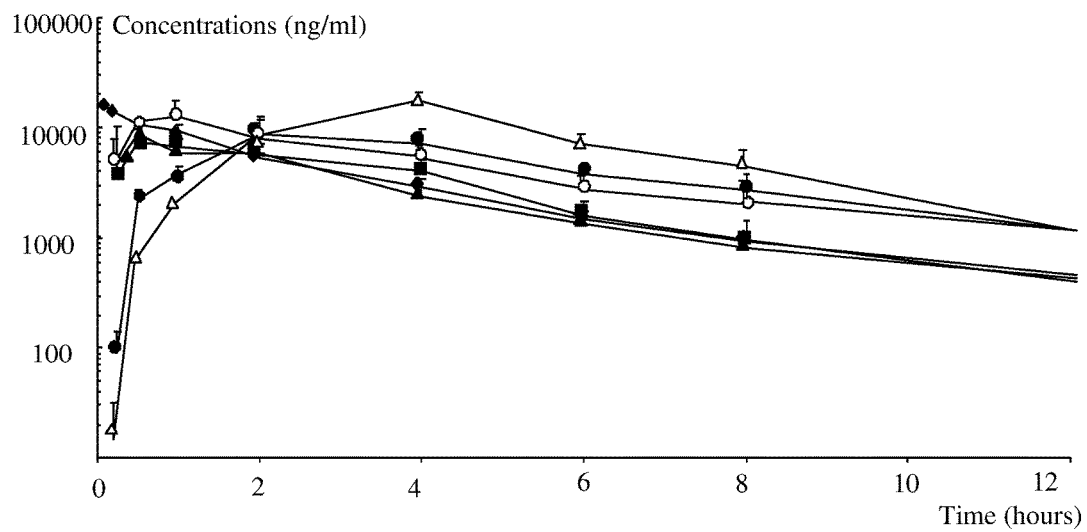
Fig. 1A
Fig. 1B
◆ Reference IV, 15 mg/kg,
△ Reference capsule, 300 mg/dog
■ Formulation 1, 20 mg/kg (10% granules)
▲ Formulation 2, 20 mg/kg (5.8% granules)
○ Formulation 3, 200 mg/dog (Dispersible tablets)
● Formulation 4, 200 mg/dog (Conventional tablets)

Schematic TLC profile of the collected fractions

ORAL FORMULATIONS OF PYRROLIDINE DERIVATIVES

TECHNICAL FIELD

The present invention relates to solid oral formulations comprising a compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, and the use of said formulations in the treatment and/or prevention of preterm labor, premature birth, dysmenorrhea and embryo implantation failure due to uterine contractions. The present invention is furthermore related to processes for their preparation.

BACKGROUND OF THE INVENTION

Oxytocin (OT) is a cyclic nona-peptide that mediates its physiological actions through activation of the oxytocin receptor (GT-R), a cell membrane receptor belonging to the class of G protein-coupled receptors that is similar to arginine vasopressin receptors. One important action of OT is to cause the contraction of the uterus of mammals during labor. Repeated, concerted and regular contraction of the uterus will cause the dilatation of the cervix, the rupture of foetal membranes and lead to expulsion of the foetus. Premature labor is when these contractions occur before the normal term of pregnancy. Preterm increase of uterine activity is the most common expression of preterm labor.

Premature labor leads to undesired premature birth, a serious health problem that remains the major cause of perinatal mortality and severe morbidity, especially respiratory distress syndrome, intraventricular haemorrhage, bronchopulmonary dysplasia and necrotising enterocolitis that are far more common in preterm than in term infants. Long-term impairments such as cerebral palsy, visual impairment and hearing loss are also more common in preterm infants. Nowadays, preterm birth remains the leading cause of infant mortality and morbidity in industrialized nations, where, despite the significant improvements in obstetrical medicine, it is causing high costs for neonatal intensive care of premature babies. The actual costs are even higher to society when taking into consideration the healthcare provision of preterm childbirth-related ailments, such as respiratory distress syndrome, heart conditions, cerebral palsy, epilepsy, and severe learning disabilities. The management of preterm labor represents a significant problem in the field of obstetrics.

The OT/OT-R system plays a vital role in initialing labor in mammals, in particular in humans. The density of OT-R increases markedly in the myometrium before the onset and during labor. Also it is thought that the local OT peptide hormone concentration increases markedly before parturition in human. The high circulating concentrations of progesterone induce uterine quiescence while the uterus acquires contractile ability. Shortly before term, plasma progesterone concentrations fall, OT-R expression in the uterus increases markedly, OT is released and uterine contractile activity increases. At term, the contractions rise to a crescendo, resulting in delivery as a result of two interacting positive feedback loops. The first is a local uterine loop: within the uterus itself, contractile prostaglandins are produced and released in response to OT and uterine contractions. These prostaglandins may play a further role in cervical ripening and weakening of fetal membranes. The second loop involves the hypothalamus: in response to uterine contractions and vaginal and cervical distension, magnocellular oxytocin neurons in the hypothalamus increase their activity resulting in the release of OT from their axon terminals in the posterior pituitary. The released OT acts upon the uterus both to stimulate the further production of prostaglandins and to contribute further to the contractions of the uterus.

Therefore, blocking the effect of OT by antagonizing OT-R might represent an attractive modality for the treatment of diseases related to the OT-R activity, in particular preterm labor, premature birth and dysmenorrhea.

Tocolytic, i.e. uterus relaxing agents, have been used in clinical studies for the pharmaceutical treatment of preterm labor. Most of these agents are used off-label. They have shown very limited efficacy, if any, in prolonging gestation and without clear demonstration of improvement of neonate outcome. Current tocolytics are very often associated with unwanted adverse effects on women, foetus or neonate. Such tocolytics include beta-2-adrenergic agonists, prostaglandin synthesis inhibitors, magnesium sulfate, nitric acid donors and calcium channel blockers. Beta-2-adrenergic agonists such as ritodrine or terbutaline cause a number of cardiovascular and metabolic side effects including maternal tachycardia, palpitations, hypotension, altered thyroid function and fetal and neonatal hypoglycaemia, tachycardia. Ritodrine is no longer FDA approved. The calcium channel blocker nifedipine is also a medicine that is used to try to stop contractions. Some of the side effects that may occur include facial flushing, headache, nausea, palpitations, and lightheadedness. The total prostaglandin synthesis inhibitor (NSAID) indomethacin has been used. It can also have serious effects on the fetus: constriction of ductus arteriosus, pulmonary hypertension, decrease in renal function with oligohydramnios, intraventricular hemorrhage, hyperbilirubinemia, necrotizing enterocolitis. Maternal side effects include abdominal discomfort, nausea, vomiting, depression and dizzy spells for the mother. Another NSAID is sulindac that, has a side effect profile similar to indomethacin. For magnesium sulfate, meta-analyses have tailed to support it as a tocolytic agent. Women reported important side effects such as flushing, lethargy, headache, muscle weakness, pulmonary edema and cardiac arrest. A newborn that has been exposed to magnesium sulfate may show lethargy, hypotonia, respiratory depression, bone problems, osteopenia and fractures. Recently, the FDA is advising healthcare professionals against using magnesium sulfate injection for longer than 5-7 days to stop preterm labor in women.

Atosiban, a dual vasopressin V1a receptor and OT-R antagonist is marketed in EU and used to stop contractions and delay preterm delivery by a few days. The principal drawback to the use of peptide antagonists like Atosiban is the problem of low oral bioavailability resulting from intestinal degradation. Hence, they must be administered parenterally.

The development of orally active small molecule antagonists that are selective for the OT-R is expected to overcome these problems. Pyrrolidine derivatives being OT-R antagonists are disclosed in WO 01/72705, WO 02/102799, WO 2002/074741, and WO 2004/005249.

Thus, in the management of preterm labor and premature birth, there is a need for an oral formulation which is convenient to administer, which is suitable for providing a fast onset of action and which provides a good bioavailability of a compound being an OT-R antagonist.

SUMMARY OF THE INVENTION

The present invention provides a dispersible tablet comprising a compound of formula formula (3Z,5S)-5-(hydroxymethyl)-1-[(2'-methyl-1,1'-biphenyl-4-yl)carbonyl]pyrrolidin-3-one-O-methyloxime, and at least one or more pharmaceutically acceptable excipients.

The invention also provides said dispersible tablet, for use in the treatment and/or prevention of disorders selected from the group comprising preterm labor, premature birth, embryo implantation failure due to uterine contractions, dysmenorrhea, premature ejaculation, sexual dysfunction, endometriosis, infertility, benign prostatic hyperplasia, neuro-psychiatric disorders, autism, social behavior disorders, psycho-social stress, and/or cardiovascular disorders.

Also provided is a process for the preparation of said dispersible tablet characterized by a step of wet granulation.

The invention further provides a kit comprising said dispersible tablet, and information for use thereof.

BRIEF DESCRIPTION OF THE FIGURES

FIGS. 1A and 1B: Plasma concentration profiles of solid oral formulations in the dog. FIG. 1A shows the plasma concentration (ng/ml) vs. time profile of formulations 1 (10% granules), 2 (5.8% granules), 3 (dispersible tablets) and 4 (conventional tablets) over the time period from 0 to 72 h. FIG. 1B shows an enlargement of FIG. 1A for the period from 0 to 12 h.

DETAILED DESCRIPTION OF THE INVENTION

Figure 2:
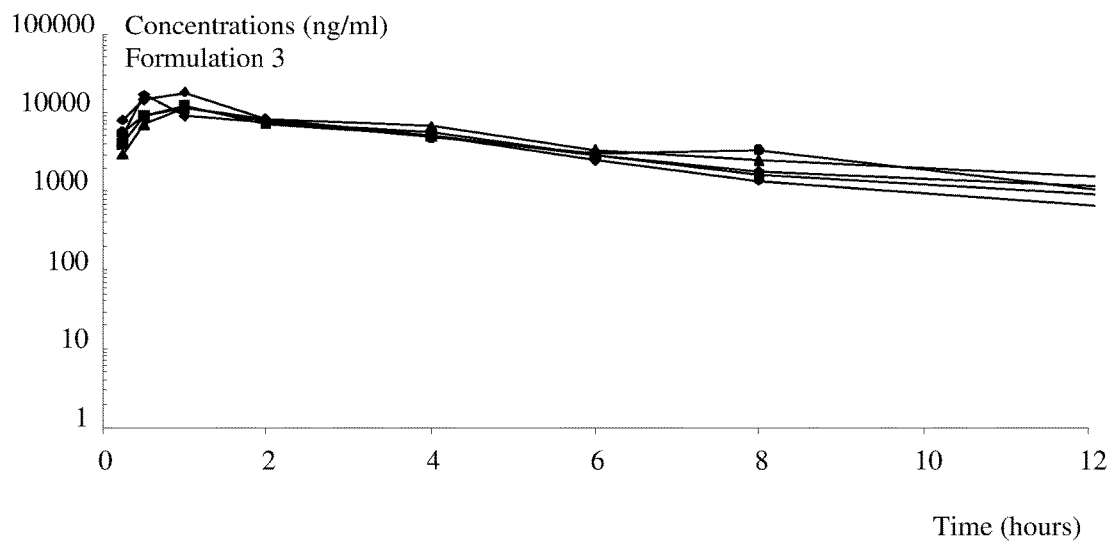
FIG. 2: Individual plasma concentration profiles of formulation 3 (dispersible tablets) in the dog. Plasma concentration of the compound of formula (3Z,5S) is measured (ng/ml) for each dog (n=5) for the time period from 0 to 12 h.

Generally, the present invention relates to a solid oral formulation comprising a compound of formula 5-(hydroxymethyl)-1-[(2'-methyl-1,1'-biphenyl-4-yl)carbonyl]pyrrolidin-3-one-O-methyloxime, its geometrical isomers, its optically active forms as enantiomers, diastereoisomers, mixtures of these, its racemate forms as well as active metabolites thereof and at least one or more pharmaceutically acceptable excipients.

Preferably, the present invention relates to a solid oral formulation comprising a compound of formula (3Z/E,5S)-5-(hydroxymethyl)-1-[(2'-methyl-1,1'-biphenyl-4-yl)carbonyl]pyrrolidin-3-one-O-methyloxime, and/or an active metabolite thereof and at least one of more pharmaceutically acceptable excipients.

Even more preferably, the present invention relates to a solid oral formulation comprising a compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, and at least one or more pharmaceutically acceptable excipients.

The compound of formula (3Z,5S)-5-(hydroxymethyl)-1-[(2'-methyl-1,1'-biphenyl-4-yl)carbonyl]pyrrolidin-3-one-O-methyloxime also named (3Z,5S) herein is produced by methods such as those disclosed for example in WO2004/005249 and WO2005/082848.

Usually, said compound is synthesized and obtained in isomeric mixtures (3Z,5S)-5-(hydroxymethyl)-1-[(2'-methyl-1,1'-biphenyl-4-yl)carbonyl]pyrrolidin-3-one-O-methyloxime comprising (3Z,5S)-5-(hydroxymethyl)-1-[(2'-methyl-1,1'-biphenyl-4-yl)carbonyl]pyrrolidin-3-one-O-methyloxime and (3Z,5S)-5-(hydroxymethyl)-1-[(2'-methyl-1,1'-biphenyl-4-yl)carbonyl]pyrrolidin-3-one-O-methyloxime.

In case the isomer Z is preferred, then the compound of formula (3Z,5S)-5-(hydroxymethyl)-1-[(2'-methyl-1,1'-biphenyl-4-yl)carbonyl]pyrrolidin-3-one-O-methyloxime synthesized and obtained in isomeric mixtures is purified according to methods disclosed in PCT/EP2014/066075.

Thus, the purity of the compound (3Z,5S)-5-(hydroxymethyl)-1-[(2'-methyl-1,1'-biphenyl-4-yl)carbonyl]pyrrolidin-3-one-O-methyloxime in said isomeric mixtures is at least 85% to 100%, preferably 85% to 99.9%: more preferably 90% to 99.9%, and even more preferably 95% to 99.9%.

Alternatively, the present invention relates to a solid oral formulation comprising a compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof provided in substantially pure form, and at least one or more pharmaceutically acceptable excipients.

As used herein, the term "substantially pure" refers to a compound provided in a form which is substantially free of other compounds. Examples of said "other compounds" include formula (3E,5S)-5-(hydroxymethyl)-1-[(2'-methyl-1,1'-biphenyl-4-yl)carbonyl]pyrrolidin- 3-one-O-methyloxime, (3Z,5S)-5-(hydroxymethyl)-1-[(2'-methyl-1,1'-biphenyl-4-yl)carbonyl]pyrrolidin-3-one, (3Z,5S)-5-(hydroxymethyl)-1-[(2'-methyl-1,1'-biphenyl-4-yl)carbonyl]pyrrolidin-3-one oxime, (3R,5S)-5-(hydroxymethyl)-1-[(2'-methyl-1,1'-biphenyl-4-yl)carbonyl]-3-methoxyamino-pyrrolidine, (3S,5S)-5-(hydroxymethyl)-1-[(2'-methyl-1,1'-biphenyl-4-yl)carbonyl]-3-methyloxyamino-pyrrolidine, (3Z,5S)-5-(O-[(2'-methyl-1,1'-biphenyl-4-yl)carbonyl]pyrrolidin-3-one-O-methyloxime and (3E,5S)-5-(O-[(2'-methyl-1,1'-biphenyl-4-yl)carbonyl]pyrrolidin-3-one-O-methyloxime.

Most preferably, the compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof is substantially free of the compound of formula (3E,5S)-5-(hydroxymethyl)-1-[(2'-methyl-1,1'-biphenyl-4-yl)carbonyl]pyrrolidin-3-one-O-methyloxime.

Even more preferably, the purity of a substantially pure form compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, is at least 55%, at least 60%, at least 65%, at least 70%, at least 75%, at least 80%, at least 85%, at least 90%, at least 95%, at least 98%, at least 99%, at least 99.2%, at least 99.3%, at least 99.4%, at least 99.5%, at least 99.6%, at least 99.7%, at least 99.8%, at least 99.9% or at least 100% and is therefore substantially free of compound of formula (3E,5S)-5-(hydroxymethyl)-1-[(2'-methyl-1,1'-biphenyl-4-yl)carbonyl]pyrrolidin-3-one-O-methyloxime.

Even more preferably, the purity of the substantially pure form compound of formula (3Z,5S)-5-(hydroxymethyl)-1-[(2'-methyl-1,1'-biphenyl-4-yl)carbonyl]pyrrolidin-3- one-O-methyloxime, and/or an active metabolite thereof, is at least in the range of 85% to 100%, preferably 85% to 99.9%, more preferably 90% to 99.9%, and even more preferably in the range of 95% to 99.9%.

As used herein, the term "active metabolite thereof" refers to a product produced through metabolism in the body, or in vitro, of a specified compound, i.e. in the present case (3Z,5S)-5-(hydroxymethyl)-1-[(2'-methyl-1,1'-biphenyl-4-yl)carbonyl]pyrrolidin-3-one-O-methyloxime, and which exhibits the same biological activity as (3Z,5S)-5-(hydroxymethyl)-1-[(2'-methyl-1,1'-biphenyl-4-yl)carbonyl]pyrrolidin-3-one-O-methyloxime.

Active metabolites of (3Z,5S)-5-(hydroxymethyl)-1-[(2'-methyl-1,1'-biphenyl-4-yl)carbonyl]pyrrolidin-3-one-O-methyloxime may be identified using routine techniques known in the art and their activities determined using tests such as those described herein. Such metabolites may result for example from the oxidation, glucuronidation or other conjugation, hydrolysis, reduction and the like, of the administered Z form. Accordingly, the invention includes active metabolites of (3Z,5S)-5-(hydroxymethyl)-1-[(2'-methyl-1,1'-biphenyl-4-yl)carbonyl]pyrrolidin-3-one-O-methyloxime, including compounds produced by a process comprising contacting a compound of this invention with a mammal for a period of time sufficient to yield a metabolic product thereof. Such metabolite may also be produced in vitro by oxidation, reduction, hydrolysis, glucuronidation or other conjugation transformation of the corresponding (3Z,5S)-5-(hydroxymethyl)-1-[(2'-methyl-1,1'-biphenyl-4-yl)carbonyl]pyrrolidin-3-one-O-methyloxime. Examples of actives metabolites of (3Z,5S)-5-(hydroxymethyl)-1-[(2'-methyl-1,1'-biphenyl-4-yl)carbonyl]pyrrolidin-3-one-O-methyloxime, include compounds whose structures are shown below:

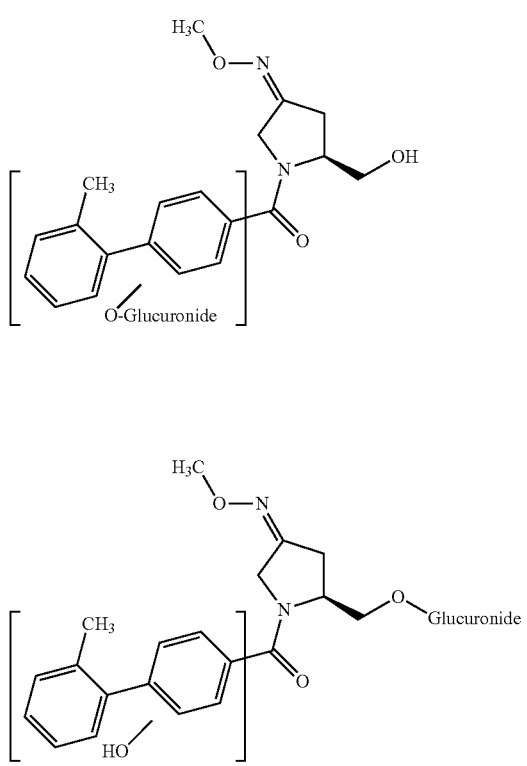

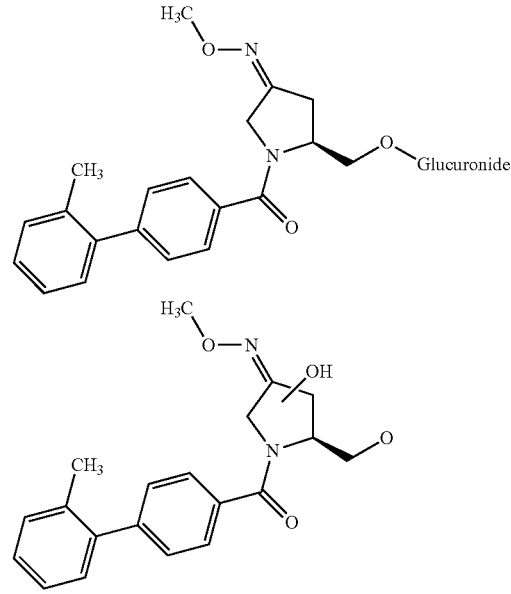

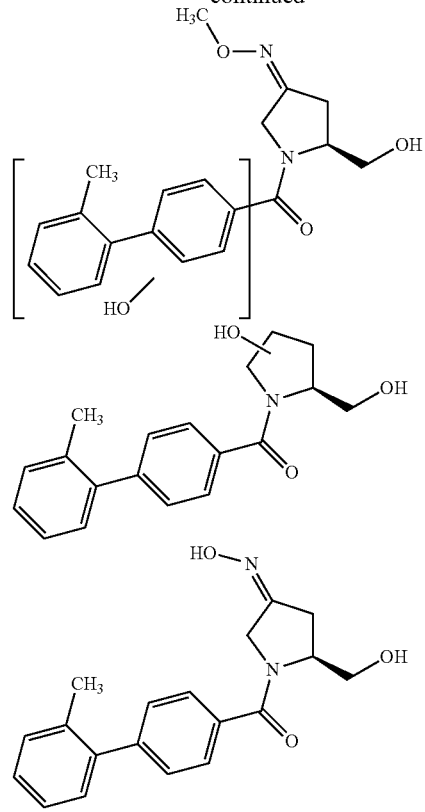

A compound which, upon administration to the recipient, is capable of being converted into a compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof as described above, is known as a "prodrug". A prodrug may, for example, be converted within the body, e.g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976): "Design of Prodrugs" ed. H. Bundgaard, Elsevier, 1985; and in Edward B. Roche, ed., Bioreversible Carriers in Drug Design, American Pharmaceutical Association and Pergamon Press, 1987, which disclosures are incorporated herein by reference.

As used herein, die term "solid oral formulation" refers to a tablet, a dispersible tablet, a last dissolving tablet a quick dissolving tablet, a last melt tablet a mouth-dissolving tablet, a melt-in mouth tablet, an orodispersible tablet, a lyophilised unit, a porous tablet a conventional tablet, a coated tablet, an uncoated tablet a gastro-resistant tablet, an effervescent tablet, a soluble tablet, a chewable tablet, an oral lyophilisate, a powder, an oral powder, a pellet, a capsule and/or a granule. Preferably, the solid oral formulation is a tablet, more preferably, a dispersible tablet.

As used herein, the term "dispersible tablet" includes a disintegrating tablet that is swallowed, or intended to be disintegrated rapidly in water and to be swallowed.

As used herein, "pharmaceutically acceptable excipients" includes any carriers, diluents, adjuvants, vehicles, preserving agents, antioxidant agents, fillers, bulking agent, glidant buffering agents, thickening agents, disintegrating agents, lubricants, binders, wetting agents, sweeteners, flavouring agent, taste-masking agents, emulsifying agents, suspending agents, solvents, dispersion media, coatings, antibacterial agents, anti-oxidants, antifungal agents, isotonic and absorption delaying agents and the like. The use of such media and agents for pharmaceutical active substances is well-known in the art. Except insofar as any conventional media or agent is incompatible with the active ingredient its use in the solid oral formulation is contemplated. Supplementary active ingredients can also be incorporated into the solid oral formulation as suitable therapeutic combinations.

Preferably, the dispersible tablet of the invention comprises a compound of formula (3Z,5S)-5-(hydroxymethyl)-1-[(2'-methyl-1,1'-biphenyl-4-yl)carbonyl]pyrrolidin-3-one-O-methyloxime and at least one or more pharmaceutically acceptable excipients selected from the group consisting of a disintegrant, a wetting agent, a carrier, a lubricant, a binder, a diluent, a sweetener, and a taste-masking agent.

Thus, the present invention relates to a dispersible tablet comprising a compound of formula (3Z,5S)-5-(hydroxymethyl)-1-[(2'-methyl-1,1'-biphenyl-4-yl)carbonyl]pyrrolidin-3-one-O-methyloxime, and a disintegrant. For example, the "disintegrant" may be selected from one of the group consisting of sodium croscarmellose, crospovidone, sodium alginate, colloidal magnesium-aluminum silicate, calcium silicate, sodium starch glycolate, acrylic acid derivatives, microcrystalline cellulose, sodium carboxymethyl cellulose, calcium carboxymethyl cellulose, modified cellulose gum, cross-linked povidone, alginic acid and alginates, pregelatinised starch, modified corn starch and combinations thereof. Preferably, the "disintegrant" is selected from the group consisting of sodium croscarmellose, crospovidone and combination thereof. More preferably, the "disintegrant" is sodium croscarmellose.

The present invention alternatively relates to a dispersible tablet comprising a compound of formula (3Z,5S)-5-(hydroxymethyl)-1-[(2'-methyl-1,1'-biphenyl-4-yl)carbonyl]pyrrolidin-3-one-O-methyloxime, and a wetting agent. For example, the "wetting agent" may be selected from the group consisting of poloxamer, sodium lauryl sulphate, polyoxyethylene sorbitan fatty acid esters, polyoxyethylene stearate, sorbitan fatty acid esters and combinations thereof. Preferably, the "wetting agent" is selected from the group consisting of poloxamer, sodium lauryl sulfate and combination thereof. More preferably, the "wetting agent" is poloxamer 188.

Furthermore, the present invention relates to a dispersible tablet comprising a compound of formula (3Z,5S)-5-(hydroxymethyl)-1-[(2'-methyl-1,1'-biphenyl-4-yl)carbonyl] pyrrolidin-3-one-O-methyloxime, and a carrier. For example, the "carrier" may be selected from the group consisting of calcium silicate, calcium carbonate, calcium phosphate, tribasic calcium phosphate, lactose, starch, modified starch, sugars, celluloses, cellulose derivatives, polymethacrylates, chitin, chitosan and combinations thereof. Preferably, the "carrier" is selected from the group consisting of calcium silicate, calcium carbonate, calcium phosphate and combinations thereof. More preferably, the carrier is calcium silicate.

The present invention also relates to a dispersible tablet comprising a compound of formula (3Z,5S)-5-(hydroxymethyl)-1-[(2'-methyl-1,1'-biphenyl-4-yl)carbonyl]pyrrolidin-3-one-O-methyloxime, and/or a disintegrant, and/or a wetting agent, and/or a carrier. Preferably, said dispersible tablet comprises a compound of formula (3Z,5S)-5-(hydroxymethyl)-1-[(2'-methyl-1,1'-biphenyl-4-yl)carbonyl]pyrrolidin-3-one-O-methyloxime, and/or sodium croscarmellose, and/or poloxamer 188, and/or calcium silicate.

The present invention also relates to a dispersible tablet comprising a compound of formula (3Z,5S)-5-(hydroxymethyl)-1-[(2'-methyl-1,1'-biphenyl-4-yl)carbonyl]pyrrolidin-3-one-O-methyloxime and at least one or more pharmaceutically acceptable exclpients in an amount effective to provide a tablet that releases between about 90 to 100% of formula (3Z,5S)-5-(hydroxymethyl)-1-[(2'-methyl-1,1'-biphenyl-4-yl)carbonyl]pyrrolidin-3-one-O-methyloxime. A classical Pharmacopeia compliant, dissolution test (USP2) was performed. As shown in the example, a rapid dissolution profile of the dispersible tablet of 200 mg is observed at 15 min wherein the concentration of (3Z,5S) in water is between 90% to 100% of the initial concentration value (Table 30).

Preferably the one or more pharmaceutical acceptable excipients includes at least one disintegrant. More preferably, the disintegrant is selected from the group consisting of sodium croscarmellose, crospovidone and a combination thereof. More preferably, the "disintegrant" is sodium croscarmellose.

For example, the "binder" may be selected from the group consisting of polyvinylpyrrolidone, cross-linked PVP, cellulose or cellulose derivatives such as hydroxypropylmethyl cellulose (HPMC), carboxymethylcellulose sodium, ethyl cellulose, hydroxyethyl cellulose, hydroxypropyl cellulose, methyl cellulose, carboxyethylcellulose, calcium, guar gum, tragacanth, polyvinylacetates, gelatin, pregelatinised starch, starch, polyvinylalcohols, alginic acid, sodium alginate, sorbitol, glucose, magnesium aluminium silicate, dextrin, polyethylene glycol, polymethacrylates and combinations thereof.

For example, the "diluent" may be selected from the group consisting of microcrystalline cellulose, lactose monohydrate, lactose, compressible sugar, sugar, dextrose, mannitol, dextrin, maltodextrin, sorbitol, xylitol, sodium chloride, calcium carbonate, magnesium carbonate, calcium phosphate, calcium sulphate, magnesium oxide, kaolin, powdered cellulose, pregelatinized starch, starch, barium sulphate, magnesium trisilicate, aluminium hydroxide and combinations thereof. For example, the "sweetener" may be sodium saccharine, sucrose, sucralose, aspartame, sorbitol or combinations thereof.

For example, the "lubricant" may be selected from the group consisting of glycerol dibehenate, glycerol tribehenate, magnesium stearate, calcium stearate, talc, sodium stearyl fumarate, sodium behenate, stearic acid, cethyl alcohol, polyoxyethylene glycol, leucine, sodium benzoate, stearates, talc, polyethylene glycol, glyceryl monostearate, glyceryl palmitostearate, liquid paraffin, poloxamer, sodium lauryl sulphate, magnesium lauryl sulphate, hydrogenated castor oil, colloidal silicon dioxide, palmitostearate, stearic acid, zinc stearate, stearyl alcohol, hydrogenated vegetable oil and combinations thereof.

The present invention also relates to a solid oral formulation comprising a compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, and at least one or more pharmaceutically acceptable excipients, wherein the concentration of said compound and/or active metabolite thereof, is comprised between about 1% and 50% w/w. Preferably, the concentration of the compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof is 10-40% w/w, 20-30% w/w, about 20% w/w.

As used herein, the term "about" applies to numeric values and refers to a range of numbers that one of skill in the art would consider equivalent to the recited values. For example, "about 20% w/w" refers to the range 15%-25% w/w.

The present invention also relates to a solid oral formulation comprising a compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, and at least one or more pharmaceutically acceptable excipients, wherein said formulation comprises about 10 mg to about 500 mg of the compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof. Preferably, said formulation comprises about 20-400 mg or 40-200 mg of the compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof. Preferably, said formulation in the form of a dispersible tablet comprises about 50 mg or 200 mg of a compound of formula (3Z,5S)-5-(hydroxymethyl)-1-[(2'-methyl-1,1'-biphenyl-4-yl)carbonyl]pyrrolidin-3- one-O-methyloxime.

Advantageously, the present invention provides a solid oral formulation, which is i) convenient to administer, ii) suitable for providing a fast onset of action and which provides a good bioavailability of the compound of formula (3Z,5S)-5-(hydroxymethyl)-1-[(2'-methyl-1,1'-biphenyl-4-yl)carbonyl]pyrrolidin-3-one-O-methyloxime, and/or active metabolite thereof. As used herein, the term "Tmax" refers to the time to reach the peak plasma concentration (Cmax) of a drug after administration wherein the concentration is the amount of the drug in a given volume of plasma, expressed in ng/ml in the examples.

As used herein, the term "onset of action" refers to the time required after administration of a drug to become effective.

As shown in the examples, the solid oral formulations of the present invention, in particular in the form of a dispersible tablet, have the advantage of being suitable for providing a rapid onset of action. The maximum concentration in blood of the compound of formula (3Z,5S)-5-(hydroxymethyl)-1-[(2'-methyl-1,1'-biphenyl-4-yl)carbonyl]pyrrolidin-3-one-O-methyloxime, and/or active metabolite thereof, is reached at a time Tmax less than 5 h, preferably less than 1 h, more preferably less than 3 h, less than 2 h, less than 1.5 h, even more preferably less than 1 h following administration of said solid oral formulation.

Also, the maximum concentration in blood of the compound of formula (3Z,5S)-5-(hydroxymethyl)-1-[(2'-methyl-1,1'-biphenyl-4-yl)carbonyl]pyrrolidin-3-one-O-methyloxime, and/or active metabolite thereof, is reached at a time Tmax between 0.5 to 4 hours, 0.5 to 2 hours, preferably 0.5 to 1.5 hours, more preferably at a time between 0.5 to 1 hour following administration of said solid oral formulation. Preferably, said solid oral formulation is a dispersible tablet. Noteworthy, at a time of 0.5 hour following administration of the solid oral formulation, the concentration in blood of the compound of formula (3Z,5S)-5-(hydroxymethyl)-1-[(2'-methyl-1,1'-biphenyl-4-yl)carbonyl]pyrrolidin-3-one-O-methyloxime, and/or active metabolite thereof, is at least 25%, at least 35%, at least 40%, at least 45%, at least 55%, at least 65%, at least 75%, or at least 85% of Cmax. Preferably, said solid oral formulation is a dispersible tablet.

Also, at a time of 0.5 hour following administration of the solid oral formulation, the concentration in blood of the compound of formula (3Z,5S)-5-(hydroxymethyl)-1-[(2'-methyl-1,1'-biphenyl-4-yl)carbonyl]pyrrolidin-3-one-O-methyloxime, and/or active metabolite thereof, is comprised between 35% to 100%, 45% to 100%, 55% to 100% of Cmax, preferentially 57% to 92% of Cmax indicating that the solid oral formulation is suitable for providing a rapid onset of action. Preferably, said solid oral formulation is a dispersible tablet. As shown in the examples, at a time of 0.5 hour following administration of the dispersible tablet, the concentration in blood of the compound of formula (3Z,5S)-5-(hydroxymethyl)-1-[(2'-methyl-1,1'-biphenyl-4-yl)carbonyl]pyrrolidin-3-one-O-methyloxime, is comprised between 59% to 100% of Cmax in animal (Table 17), preferentially 57% to 92% of Cmax in human subjects (Table 22).

Thus, the present invention provides a solid oral formulation, preferably a dispersible tablet that is suitable for providing a rapid onset of action, which is crucial for the management of preterm labor and premature birth.

In particular, it has been shown that the maximum concentration of the active substance (3Z,5S) is detected rapidly at about 4 hours, 2 hours, 1.5 hours, or 1 hour following administration of the dispersible tablet of the present invention.

Furthermore, the solid oral formulation of the present invention is characterized by a bioavailability of the compound of formula (3Z,5S)-5-(hydroxymethyl)-1-[(2'-methyl-1,1'-biphenyl-4-yl)carbonyl]pyrrolidin-3-one-O-methyloxime, and/or active metabolite thereof, comprised between 50-100%, and/or 50-99%. Preferably, said bioavailability is comprised between 75-100%, or 75-99%, more preferably, between 80-100%, or 80-99%. As used herein, the term "bioavailability" (F %) refers to the fraction of an administered dose of a product that reaches the systemic circulation. By definition, when the product is administered intravenously, its bioavailability is 100%. When the product is administered via other routes, its bioavailability generally decreases.

As shown in the examples, the bioavailability (F %) of the solid oral formulations of the present invention, is comprised between 58% and 90% (Table 16). In particular, the bioavailability of the solid oral formulation in the form of a dispersible tablet is comprised between 80% and 190% (Table 18, 102% in table 18 is indicated as 100% based on the standard deviation).

In particular, it has been shown that the bioavailability of the active substance (3Z,5S) is about 89% following administration of the dispersible tablet of the present invention (Table 16).

Advantageously, patients administered with the solid oral formulation of the present invention will benefit from a fast onset of action and/or a good bioavailability.

Also, the present invention provides a solid oral formulation comprising:
20% by weight of a compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof;
1-20% by weight of calcium silicate;
0.1-20% by weight of PVP30K;
0.01-5% by weight of poloxamer 188;
0.5-20% by weight of sodium croscarmellose;
1-90% by weight of microcrystalline cellulose 112;
1-90% by weight of lactose monohydrate:
0.01-0.5% by weight of sodium saccharine; and
0.3-10% by weight of glycerol dibehenate.

Alternatively, the present invention provides a dispersible tablet comprising 20% by weight of a compound of formula (3Z,5S)-5-(hydroxymethyl)-1-[(2'-methyl-1,1'-biphenyl-4-yl)carbonyl]pyrrolidin-3-one-O-methyloxime, and 0.5-20% by weight of a disintegrant. Preferably said disintegrant is sodium croscarmellose.

Also alternatively provided is a dispersible tablet comprising 20% by weight of a compound of formula (3Z,5S)-5-(hydroxymethyl)-1-[(2'-methyl-1,1'-biphenyl-4-yl)carbonyl]pyrrolidin-3-one-O-methyloxime, and 1-20% by weight of a carrier. Preferably, said carrier is calcium silicate.

Alternatively, it further provides a dispersible tablet comprising 20% by weight of a compound of formula (3Z,5S)-5-(hydroxymethyl)-1-[(2'-methyl-1,1'-biphenyl-4-yl)carbonyl]pyrrolidin-3-one-O-methyloxime, and 0.01-5% by weight of a wetting agent. Preferably, said wetting agent is poloxamer 188.

Preferably, said solid oral formulation consists of:
20% by weight of a compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof.
5% by weight of calcium silicate,
1% by weight of PVP30K,
2% by weight of Poloxamer 188,
5% by weight of Sodium croscarmellose,
15% by weight of Microcrystalline cellulose 112,
47.8% by weight of Lactose monohydrate,
0.2% by weight of Sodium saccharine and
4% by weight of Glycerol dibehenate.

Whilst the compound formula (3Z,5S)-5-(hydroxymethyl)-1-[(2'-methyl-1,1'-biphenyl-4-yl)carbonyl]pyrrolidin-3-one-O-methyloxime, and/or the active metabolite thereof may be used as the sole active ingredient of the solid oral formulation, it is also possible for the compound to be used in combination with at least one or more further active compounds. Such further active compounds may be further compounds according to the invention, or other active compounds selected horn the group comprising calcium channel blockers, magnesium sulfate, selective prostaglandin modulators, beta-2-adrenergic agonists, beta-3-adrenergic receptor agonists, and/or corticosteroids.

Preferably, corticosteroids are selected from the group comprising Betamethasone and Dexamethasone, and/or salts thereof. These corticosteroids are given before birth to accelerate a preterm fetus' lung development and maturation to prevent respiratory distress syndrome (RDS) and other related complications following premature birth.

Alternatively, the solid oral formulation of the invention can be administered concomitantly or separately with at least one compound selected from the group comprising calcium channel blockers (such as nifedipine), magnesium sulfate, prostaglandin receptors modulators (such as agonists or antagonists of either EP1 or EP2 or EP3 or EP4 or FP receptors), prostaglandin synthesis inhibitors (such as indomethacin, nimesulide, sulindac, rofecoxib, celecoxib), beta-2-adrenergic agonists (such as ritodrine, terbutaline, salbutamol), beta-3-adrenergic receptor agonists, nitric field donors (such as glyceryl trinitrate) and/or corticosteroids (such as dexamethasone, betamethasone).

As used herein, the term "concomitantly" refers to the administration of a solid oral formulation comprising a compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, which is then immediately followed by the administration of at least one compound selected from the group disclosed supra.

As used herein, the term "separately" encompasses sequential or subsequent administration and refers to the administration of a solid oral formulation of the invention comprising the compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, followed by a time period of discontinuance, which is then followed by the administration of at least one compound disclosed supra.

The compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, is an oxytocin receptor antagonist.

As used herein, the term "oxytocin receptor antagonist" refers to a compound that functions by inhibiting (partially or completely) or blocking the oxytocin receptor (OT-R), thereby preventing activation of the receptor by oxytocin.

Generally, the compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, is a vasopressin V1a receptor antagonist.

As used herein, the term "vasopressin V1a receptor antagonist" refers to a compound that functions by inhibiting (partially or completely) or blocking the vasopressin V1a receptor (also known as Arginine vasopressin receptor 1A), thereby preventing activation of the receptor by vasopressin. Vasopressin V1a receptor is one of the three major receptor types for the peptide hormone arginine vasopressin, the others being V1b and V2 receptors.

Hence, the present invention relates to a solid oral formulation comprising a compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, and at least one or more pharmaceutically acceptable excipients, wherein said compound is an oxytocin receptor antagonist and/or a vasopressin V1a receptor antagonist.

Disorders associated with the oxytocin receptor activity and/or vasopressin V1a receptor activity are selected from the non-limiting group comprising preterm labor, premature birth, embryo implantation failure due to uterine contractions, dysmenorrhea, premature ejaculation, sexual dysfunction, endometriosis, infertility, benign prostatic hyperplasia, neuro-psychiatric disorders, autism, social behavior disorders, psycho-social stress, and/or cardiovascular disorders.

The term "preterm labor" referring also to "premature labor", shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" refers to a condition characterized by cyclic pain associated with menses during ovulatory cycles. The pain is thought to result from uterine contractions and ischemia.

The term "sexual dysfunction" refers to any disturbance or variation in the four phases—excitement phase, plateau phase, orgasmic phase and resolution phase characterizing the human sexual response.

The term "neuro-psychiatric disorders" as used herein refers to mental disorders attributable to diseases of the nervous system, e.g. depression, obsessive-compulsive disorder and others.

The term "social behavior disorders" as used herein refers to emotional disturbance, inappropriate types of behavior or feelings, pervasive mood of unhappiness or depression and a range of perceived difficulties to build or maintain satisfactory interpersonal relationships The term "psycho-social stress" as used herein refers to a condition resulting from a perceived threat to the social status, social esteem, self-worth, respect or acceptance within a group, and that lead to development of a stress response in the body and physical symptoms.

Assisted reproduction technologies are methods applied in humans for the treatment of infertility and in animals for producing pregnancies. Infertility, which affects about 10% of human pairs worldwide, may be treated by in vitro fertilization and embryo transfer (IVF-ET) or in less complicated cases, by artificial insemination. Generally, a success of an embryo transfer is dependent on uterine receptivity, an entity that is defined as an ability of uterus to provide optimal conditions mandating proper implantation and embryo development. Basic components of uterine receptivity are uterine contractile activity and the condition of endometrium.

Uterine contractions occurring during the embryo transfer may expel embryos from the uterus towards vagina or oviducts, which may be a cause of unsuccessful treatment or in latter case a cause of extra uterine pregnancy, a serious, potentially life-threatening complication.

Hence, the present invention provides a solid oral formulation, for use in the treatment and/or prevention of disorders selected from the group comprising preterm labor, premature birth, dysmenorrhea, premature ejaculation, sexual dysfunction, endometriosis, embryo implantation failure due to uterine contractions, infertility, benign prostatic hyperplasia, neuro-psychiatric disorders, autism, social behaviour disorders, psycho-social stress, and/or cardiovascular disorders. Preferably, said solid oral formulation is a dispersible tablet.

Preferably, the present invention provides a solid oral formulation for use in the treatment and/or prevention of preterm labor, premature birth, dysmenorrhea and embryo implantation failure due to uterine contractions.

The present invention also provides a process for the preparation of a solid oral formulation comprising a compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, characterized by a step of wet granulation.

In wet granulation, granules are formed by the addition on powder particles of a liquid such as water, ethanol and isopropanol, either alone or in combination.

Preferably, the present invention provides a process for the preparation of a tablet comprising a compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, characterized by a step of wet granulation. More preferably, said tablet is a dispersible tablet.

Alternatively, the present invention provides a process for the preparation of a solid oral formulation comprising a compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, and at least one or more pharmaceutically acceptable excipients, characterized by the steps of: (i) mixing the compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, and at least one or more pharmaceutically acceptable excipients;
(ii) wet-granulating;
(iii) sieving the granules
(iv) blending with a lubricant such as glycerol dibehenate; and
(v) compressing the mixture obtained in step (iv) to form a tablet.

Preferably, said tablet is a dispersible tablet.

The tablet cores may vary in shape and be, for example, round, oval, oblong, cylindrical or any other suitable shape.

The present invention also provides a kit comprising a solid oral formulation comprising a compound of formula (3Z,5S)-5-(hydroxymethyl)-1-[(2'-methyl-1,1'-biphenyl-4-yl)carbonyl]pyrrolidin-3-one-O-methyloxime, and/or an active metabolite thereof, and at least one or more pharmaceutically acceptable excipients, and information for use thereof. The information contains instructions to administer the oral formulation to a subject in need thereof.

Generally, in the present invention the subject in need thereof is preferably a mammal most preferably a human, more preferably a woman.

For practical reason, the solid oral formulation of the present invention can be packaged in a unit dose. As used herein, the term "unit dose" refers to a solid oral formulation that is dispensed in a package ready to administer to the patient. Each unit dose contains a predetermined quantity of active product calculated to produce the desired therapeutic effect, in association with at least one or more suitable pharmaceutical excipients.

EXAMPLES

Z,5S)-5-(hydroxymethyl)-1-[(2'-methyl-1,1'-biphenyl-4-yl)carbonyl]pyrrolidin-3-one-O-methyloxime In the present invention, the compound of formula (3Z,5S)-5-(hydroxymethyl)-1-[(2'-methyl-1,1'-biphenyl-4-yl)carbonyl]pyrrolidin-3-one-O-methyloxime was obtained as a crude isomeric mixture comprising (3Z,5S)-5-(hydroxymethyl)-1-[(2'-methyl-1,1'-biphenyl-4-yl)carbonyl]pyrrolidin-3-one-O-methyloxime and (3E,5S)-5-(hydroxymethyl)-1-[(2'-methyl-1,1'-biphenyl-4-yl)carbonyl]pyrrolidin-3-one-O-methyloxime.

Synthetic pathways of compounds used in the invention are for example those described in WO2004005249 and WO2005082848.

The compound (3Z,5S)-5-(hydroxymethyl)-1-[(2'-methyl-1,1'-biphenyl-4-yl)carbonyl]pyrrolidin-3-one-O-methyloxime, used herein is also defined as "(4Z,2S)-2-(hydroxymethyl)-1-[(2'-methyl-1,1'-biphenyl-4-yl)carbonyl]pyrrolidin-4-one-O-methyloxime" depending on the nomenclature used.

The compound (3Z/E,5S)-5-(hydroxymethyl)-1-[(2'-methyl-1,1'-biphenyl-4-yl)carbonyl]pyrrolidin-3-one-O-methyloxime can also be prepared following stages 1 to 6 as described below:

Stage 1: Preparation of 4-(2-methylphenyl)benzoic Acid

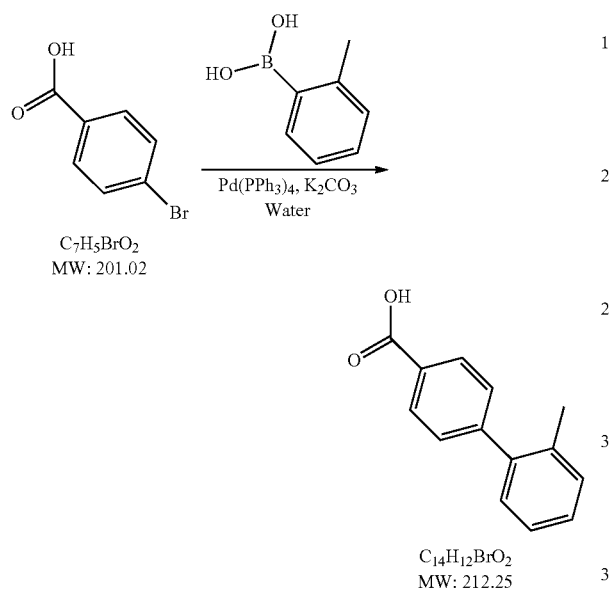

A solution of potassium carbonate (0.908 Kg, 6.57 mol, 2.06 wt) in water (2.20 L, 5.0 vol) was charged to a slurry of 4-bromobenzoic acid (0.441 Kg, 2.19 mol, 1.0 wt) in water (4.41 L, 15.0 vol) at 15 to 25° C. The resulting slurry was stirred at 15 to 25° C. and degassed three times using a vacuum-nitrogen purge cycle. Tetrakis(triphenylphosphine)palladium(0) (0.022 Kg, 0.019 mol, 0.05 wt) was charged and the vacuum-nitrogen purge cycle repeated. A solution of o-tolylboronic acid (0.313 Kg, 2.30 mol 0.707 wt) in methanol (3.53 L, 8.0 vol) was degassed three times, using a vacuum-nitrogen purge cycle, and then charged to the 4-bromobenzoic acid slurry at 15 to 25° C. The reaction mixture was heated to and maintained at reflux (71 to 78° C.) until reaction completion (The reaction is considered complete at 95% conversion), as determined by $^1$H NMR analysis (d6-DMSO), typically 1.5 to 2.5 hours. The reaction mixture was concentrated to 15 vol under vacuum at 40 to 45° C. Toluene (4.41 L, 10.0 vol) and tetrahydrofuran (4.41 L, 10.0 vol) were added to the residue, the resulting mixture stirred vigorously and acidified to pH 1 with hydrochloric acid (6M, 2.00 L, 4.5 vol). The contents were stirred vigorously for 30 to 60 minutes and the layers separated. Toluene (2.20 L, 5.0 vol) and tetrahydrofuran (2.20 L, 5.0 vol) were added to the aqueous phase and the mixture stirred for 5 to 10 minutes. The layers were separated, the combined organic phases filtered and concentrated to 10.0 vol under vacuum at 35 to 40° C. Toluene (4.41 L, 10.0 vol) was added to the residue and the resultant concentrated under vacuum at 35 to 40° C. The tetrahydrofuran content of the resulting slurry was determined by 1H NMR analysis (d6-DMSO) (Pass level; ≤1.0% w/w tetrahydrofuran with respect to toluene). The slurry was cooled to and aged at 0 to 5° C. for 30 to 60 minutes, the solid collected by filtration and the filter-cake washed with toluene (2.20 L, 5.0 vol). The solid was dried in a vacuum oven at 35 to 40° C. to give 4-(2-methylphenyl)benzoic acid [0.438 Kg, 94.1% th, 99.3% w/w, 1H NMR (d6-DMSO) concordant with structure] as a pale yellow solid.

Stage 2: Preparation of 4-(2-methylphenyl)benzoic Acid Chloride

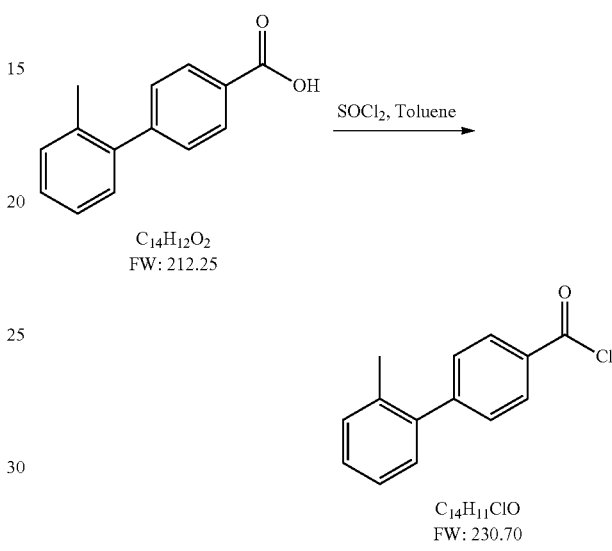

Thionyl chloride (0.300 L, 4.11 mol, 0.685 vol) was added to a slurry of 4-(2-methylphenyl)benzoic acid (0.435 Kg, 2.05 mol, 1.0 wt) in toluene (4.35 L, 10.0 vol) at 10 to 25° C. and the mixture heated to and maintained at 75 to 80° C.3 until complete by 1H NMR analysis (d6-benzene), typically 4 to 5 hours. Reaction completion was accompanied by the formation of a hazy solution. The resultant was concentrated to 5.0 vol by removal of toluene under reduced pressure at 35 to 45° C. Toluene (2.18 L, 5.0 vol) was added to the concentrate and the mixture concentrated to 4.0 vol by removal of toluene under reduced pressure at 35 to 45° C. The resultant was filtered through glass microfibre paper and the filter-cake washed with toluene (0.44 L, 1.0 vol). The toluene solution of 4-(2-methylphenyl)benzoic acid chloride [0.439 Kg, 92.8% th, 100.9% w/w, 1H NMR (d6-benzene) concordant with structure] was used directly in Stage 3.

Stage 3: Preparation of (4R)-4-hydroxy-1-[(2'-methyl-1,1'-biphenyl-4yl)-carbonyl]-L-proline

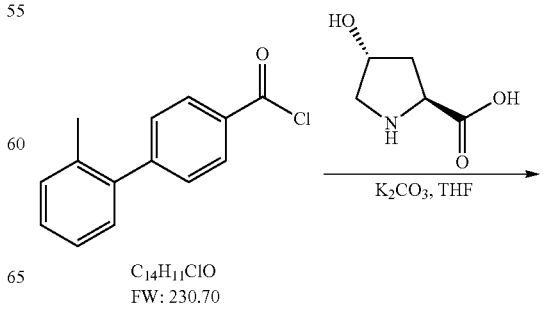

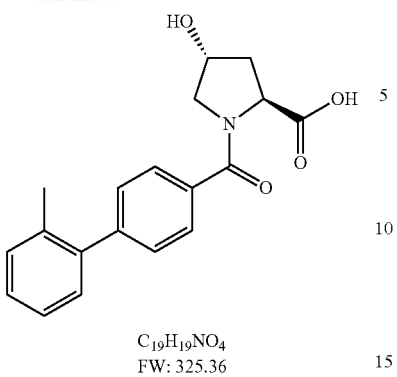

C₁₉H₁₉NO₄
FW: 325.36

A solution of potassium carbonate (0.526 Kg, 3.81 mol, 1,2 wt) in water (0.57 L, 1.3 vol) was charged to a solution of 4-hydroxy-L-proline (0.27 Kg, 2.09 mol, 0.625 wt) in tetrahydrofuran (2.20 L, 5.0 vol) and water (0.44 L, 1.0 vol) at 1.5 to 25° C. followed by a line rinse of water (0.44 L, 1.0 vol). The mixture was cooled to 0 to 5° C. with rapid stirring and a solution of 4-(2-methylphenyl)benzoic acid chloride (0.438 Kg, 1.90 mol, 1.0 wt) in toluene (2.19 L, 5.0 vol) charged at that temperature followed by a line rinse of toluene (0.44 L, 1.0 vol). The reaction mixture was warmed to 15 to 25° C. over 1 to 2 hours and stirred at this temperature until judged complete by TLC analysis. Water (2.20 L, 5.0 vol) was charged to the reaction mixture at 15 to 25° C. and the layers separated. The aqueous phase was acidified to pH 5 to 6 with aq. hydrochloric acid (6M, 0.66 L, 1.5 vol) and then to pH1 with aq. hydrochloric acid (2M, 0.88 L, 2.0 vol) at 15 to 25° C. The mixture was cooled to and aged at 0 to 5° C. for 30 to 60 minutes, the precipitated solid collected by filtration, the filter-cake washed with water (2×1.75 L, 2×4.0 vol) and toluene (0.88 L, 2.0 vol) and pulled dry on the filter for 12 to 24 hours. The collected solid was dried under vacuum at 40 to 45° C. until the water content by KF was ≤0.2% w/w to afford (4R)-4-hydroxy-1 [2'-methyl-1,1'-biphenyl-4-yl)carbonyl]-L-proline [0.599 Kg, 97.0% th, 136.8% w/w, ¹H NMR (d₆-DMSO) concordant with structure] as an off-white solid.

Stage 4: Preparation of 1-(2'-methyl-1,1'-biphenyl-4-yl)carbonyl-4-oxo-L-proline

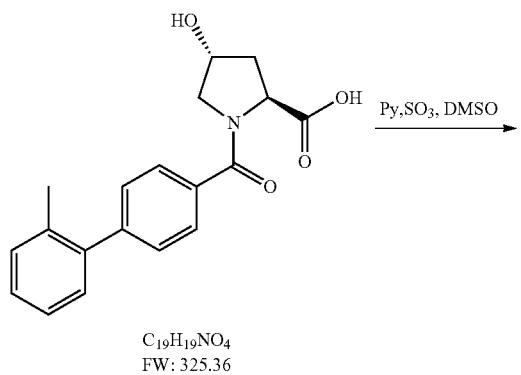

C₁₉H₁₉NO₄
FW: 325.36

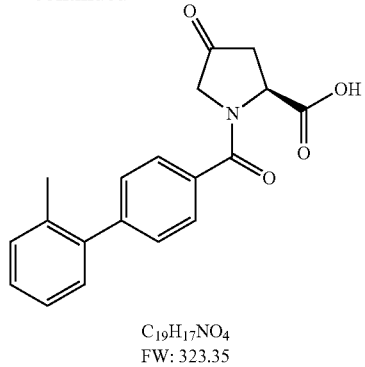

C₁₉H₁₇NO₄
FW: 323.35

Triethylamine (1.80 L, 13.56 mol, 3.0 vol) was charged to a solution of (4R)-4-hydroxy-1-[(2'-methyl-1,1'-biphenyl-4-yl)carbonyl]-L-proline (0.598 Kg, 1.84 mol, 1.0 wt) in dimethyl sulfoxide (4.42 L, 7.4 vol) at 15 to 20° C. Pyridine-sulphur trioxide complex (0.879 Kg, 5.52 mol, 1.47 wt) was charged portion-wise at 15 and 25° C. and the reaction mixture stirred at that temperature until reaction completion, as determined by TLC analysis (typically 1 to 3 hours), 7 The reaction was quenched with aq. hydrochloric acid (3M, 4.80 L, 8.0 vol) at 0 to 30° C., tetrahydrofuran (3.00 L, 5.0 vol) and heptanes (0.60 L, 1.0 vol) charged, the layers separated and the aqueous phase extracted with tetrahydrofuran (2×3.00 L, 2×5.0 vol). The combined organic phases were washed with aq. hydrochloric acid (1 M, 2×1.20 L, 2×2.0 vol) and saturated sodium chloride solution (2×1.20 L, 2×2.0 vol), the aqueous washes combined and back-extracted with tetrahydrofuran (2×0.60 L, 2×1.0 vol. The combined organics were dried over magnesium sulphate (1.794 Kg, 3.0 wt.), filtered, the filtercake washed with tetrahydrofuran (0.60 L, 1.0 vol) and the filtrates concentrated under vacuum at 40 to 45° C. to give a pale brown foam. Ethyl acetate (6.00 L, 10.0 vol) was charged to the foam, the contents stirred for 5 to 10 minutes to reach dissolution and the solvent removed under vacuum at 40 to 45° C. This was repeated using ethyl acetate (6.00 L, 5.0 vol) until tetrahydrofuran was not detected by ¹H NMR analysis (d₆-DMSO). The residue was slurried in ethyl acetate (4.80 L, 8.0 vol), activated carbon (0.084 Kg, 0.14 wt) added followed by a line rinse of ethyl acetate (3.00 L, 5.0 vol), the resultant heaved to and maintained at 70 to 80° C. for 20 to 30 minutes, cooled to 40 to 55° C. and filtered through glass microfibre paper. The filter-cake was washed with ethyl acetate (1.50 L, 2.5 vol) and the combined filtrates and wash concentrated to 2.5 to 3.5 vol under vacuum at 40 to 45° C. Crystallisation commenced during the concentration. The concentrate was transferred to a suitable vessel with a line rinse of ethyl acetate (0.30 L, 0.5 vol) and heated to 70 to 80° C. Additional ethyl acetate (0.30 L, 0.5 vol) was added as necessary to achieve dissolution. Heptanes (1.80 L, 3.0 vol) was added at 70 to 80° C. and the contents allowed to cool to between 15 and 25° C. over 1 to 2 hours. The slurry was further cooled to an aged at 0 to 5° C. for 2 to 3 hours, filtered and the filtercake washed with ethyl acetate heptanes (1.1, 0.60 L, 1.0 vol) at 0 to 5° C. followed by heptanes (3.0 L, 2.5 vol). The collected solid was dried under vacuum at 40 to 45° C. to give 1-[(2'-methyl-1,1'-biphenyl-4-yl)carbonyl]-4-oxo-L-proline [0.444 Kg, 74.7% th, 74, 2% w/w, ¹H NMR (d₆-DMSO) concordant with structure] as an off-white solid.

Stage 5; Preparation of (4Z/E)-4-methoxyimino-1-[(2'-methyl-1,1'-Biphenyl-4-yl)carbonyl]-L-Proline

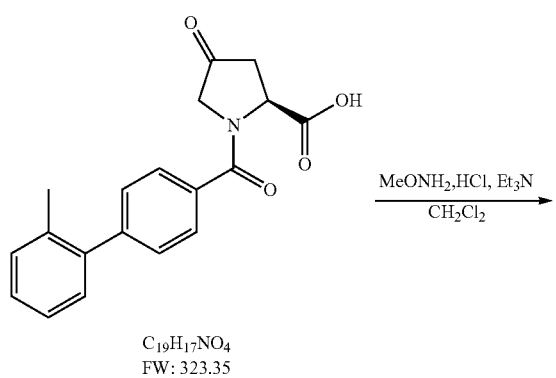

Stage 6: Preparation of (4Z/E, 2S)-methyl-1-[(2'-methyl-1,1'-biphenyl-4-yl)-carbonyl]-4-methoxyimino pyrrolidine-2-carboxylate

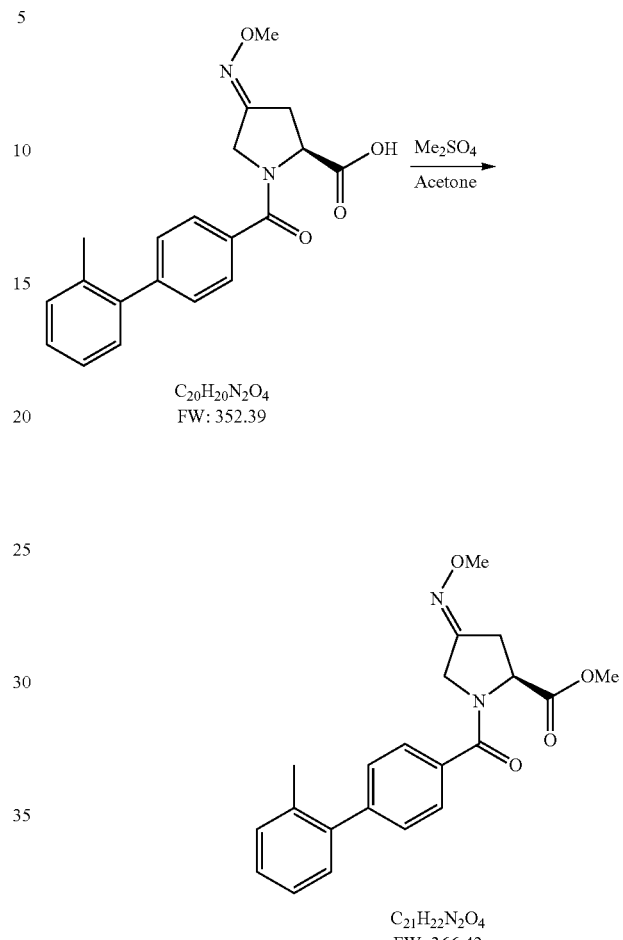

Triethylamine (0.40 L, 2.85 mol, 0.92 vol) was added to a solution of 1-[(2'-methyl-1,1'-biphenyl-4-yl)carbonyl]-4-oxo-L-proline (0.434 Kg, 1.34 mol, 1.0 wt) in dichloromethane (4.40 L, 10.0 vol) at 10 to 25° C. followed by a line rinse of dichloromethane (0.43 L, 1.0 vol). Methoxylamine hydrochloride (0.130 Kg, 1.50 mol, 0.30 wt) was added portion wise at 10 to 25° C. followed by a line rinse of dichloromethane (0.43 L, 1.0 vol) and the reaction mixture stirred at 10 to 25° C. until reaction completion, as determined by TLC analysis (typically 3 to 5 hours, TLC eluent: dichloromethane:methanol:acetic acid (90:10:1): uv visualization). The solvent was removed under vacuum at 35 to 40° C., the resultant dissolved in ethyl acetate (4.40 L, 10.0 vol) and washed with aq. hydrochloric acid (1 M, 2×2.20 L, 2×L, 5.0 vol). The acidic washes were back extracted with ethyl acetate (2.20 L, 5.0 vol), the combined organic phases washed with sat. aq. sodium chloride solution (3.10 L, 7.0 vol), dried over magnesium sulfate (0.300 Kg, 0.69 wt), filtered and the filtercake washed with ethyl acetate (2.20 L, 5.0 vol.). The filtrate and washes were combined and concentrated under vacuum at 35 to 40° C. to afford 4-methoxyimino-1-[(2'-methyl-1,1'-biphenyl-4-yl)carbonyl]-L-proline 1-[(2'-methyl-1,1'-biphenyl-4-yl)carbonyl]-L-proline 10.476 Kg, 100.6% th, 109.6% w/w, $^1$H NMR (CDCl$_3$) concordant with structure) as an off-white solid.

Potassium carbonate (0.476 Kg, 3.44 mol, 1.0 wt) was added to a solution of 4-methoxyimino-1-[(2'-methyl-1,1'-biphenyl-4-yl)carbonyl]-L-proline (0.475 Kg, 1.35 mol, 1.0 wt) in acetone (4.75 L, 10.0 vol) and the mixture cooled to 0 to 10° C. Dimethyl sulfate (0.128 L, 1.35 mol, 0.27 vol) was added at 0 to 15° C. and the mixture stirred at 15 to 25° C. until reaction completion, as determined by TLC analysis, typically 3 to 16 hours. The solvent was removed under vacuum at 40 to 45° C. and the resultant partitioned between ethyl acetate (3.80 L, 8.0 vol) and water (3.80 L, 8.0 vol). The layers were separated, the organic phase washed with sat. aq. sodium chloride solution (2.85 L, 6.0 vol), dried over sodium sulfate (0.953 Kg, 2.0 wt) and filtered. The filtercake was washed with ethyl acetate (0.48 L, 1.0 vol) and the combined filtrate and wash concentrated under vacuum at 40 to 45° C. Excess ethyl acetate was removed by azeotropic distillation with tetrahydrofuran (2×0.95 L, 2×2.0 vol) under vacuum at 40 to 45° C. to give (4Z/E, 2S)-methyl-1-[(2'-methyl-1,1'-biphenyl-4-yl)-carbonyl]-4-methoxyimino pyrrolidine-2-carboxylate [0.492 Kg, 99.6% th, 103.6% w/w, $^1$H NMR (CDCl$_3$) concordant with structure] as a viscous brown oil.

Stage 7: Preparation of (3Z/E,5S)-5-(hydroxymethyl)-1-[(2'-methyl-1,1'-biphenyl-4-yl)carbonyl]pyrrolidin-3-one-O-methyloxime

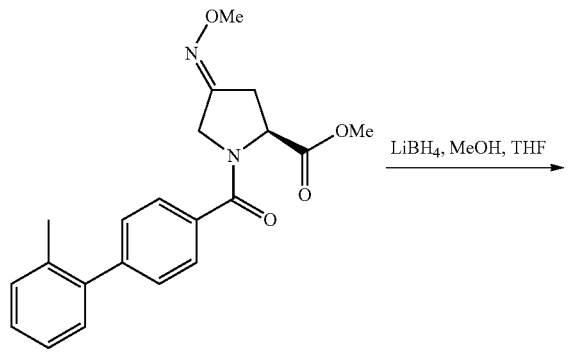

Lithium borohydride (0.049 Kg, 2.26 mol, 0.1 wt) was added portion wise under nitrogen to a stirred solution of (4Z/E,2S)-methyl-1-[(2'-methyl-1,1'-biphenyl-4-yl)carbonyl]-4-methyloximo pyrrolidine-2-carboxylate (0.492 Kg, 1.34 mol 1.0 wt) in tetrahydrofuran (2.31 L, 4.7 vol) and methanol (2.31 L, 4.7 vol) at 0 to 30° C. The mixture was stirred at 15 to 25° C. to reaction completion, as determined by TLC analysis (Eluent: ethyl acetate; Visualisation; ninhydrin), typically 2 to 6 hours. The reaction mixture was quenched with water (0.40 L, 0.8 vol) at 15 to 25° C. and stirred at 15 to 25° C. for 16 to 20 hours. The resultant was concentrated under vacuum at 40 to 45° C. and the residue partitioned between water (2.46 L, 5.0 vol) and ethyl acetate (4.92 L, 10.0 vol). The layers were separated, the organic phase washed sequentially with aq. hydrochloric acid (1M, 2.46 L, 5.0 vol), sat. aq. sodium hydrogen carbonate solution (2.46 L, 5.0 vol) and sat. aq. sodium chloride solution (2.46 L, 5.0 vol). The organic phase was dried over magnesium sulfate (0.985 Kg, 2.0 wt), filtered and the filter-cake washed with ethyl acetate (0.50 L, 1.0 vol). The combined filtrate and wash were concentrated under vacuum to give a crude isomeric mixture comprising (3Z,5S)-5-(hydroxymethyl)-1-[(2'-methyl-1,1'-biphenyl-4-yl)carbonyl]pyrrolidin-3-one-O-methyloxime and (3E,5S)-5-(hydroxymethyl)-1-[(2'-methyl-1,1'-biphenyl-4-yl)carbonyl]pyrrolidin-3-one-O-methyloxime [0.395 Kg, 86.9% th, 80.3% w/w, 1H NMR (CDCl$_3$) concordant with structure; 82.0% area by HPLC, 71.4:28.6 Z/E ratio] as a viscous brown oil. The oil was dissolved in toluene (0.40 L, 1.0 vol, with respect to weight of product) and stored until required.

Figure 4:
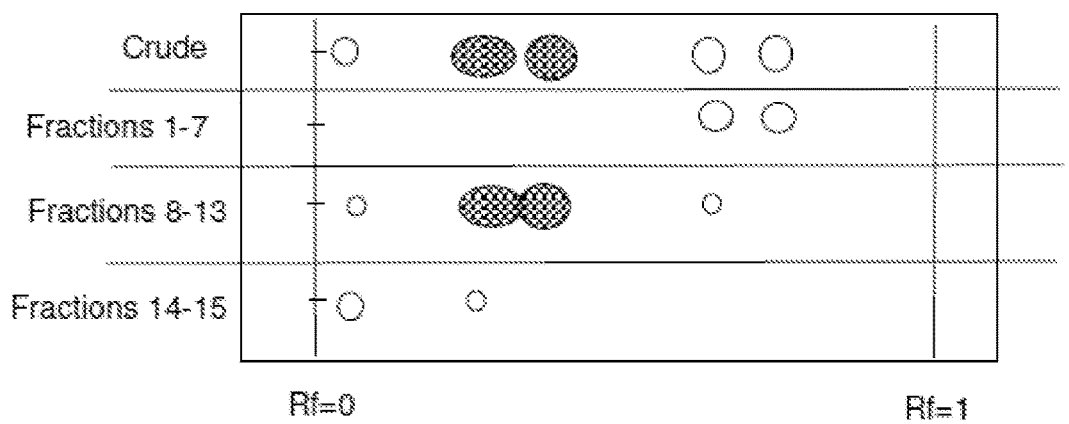
FIG. 4: Schematic TLC profile of the collected fractions from dry flash chromatography of crude (3Z/E,5S)-5-(hydroxymethyl)-1-[(2'-methyl-1,1'-biphenyl-4-yl)carbonyl]pyrrolidin-3one O-methyloxime. Fraction 1-5: eluted with pure toluene. Fractions 6-10: eluted with toluene/MeOH 1% vol/vol. Fractions 10 to 15: eluted with toluene/meOH 2% vol/vol.

1.2 Dry flash chromatography of crude formula (3Z/E,5S)-5-(hydroxymethyl)-1-[(2'-methyl-1,1'-biphenyl-4-yl)carbonyl]pyrrolidin-3-one-O-methyloxime A dry flash chromatography purification of the crude isomeric mixture obtained following the protocol described above was attempted using different elution conditions. A crude mixture of (3Z/E,5S)-5-(hydroxymethyl)-1-[(2'-methyl-1,1'-biphenyl-4-yl)carbonyl]pyrrolidin-3-one-O-methyloxime concentrated to dryness was re-dissolved in 2 volume toluene and loaded onto a pad of SiO2 (5 wt) prior to elution using 25 volume fractions of eluent. (FIG. 4)

Fractions 1-5: eluted with pure toluene

Fractions 6-10: eluted with Toluene/MeOH 1% vol/vol

Fractions 10 to 15: eluted with Toluene/MeOH 2% vol/vol

The Z and E forms are shown by shaded spots. Fractions 8 to 13 were combined and concentrated to dryness. The results show a recovery of 75%, There was no improvement in the E/Z ratio. A minor gain of about 4% area in purity of the isomeric mixture (E+Z) was observed before and after dry-flash chromatography (Table 1).

TABLE 1

Comparative impurity profile before and after dry-flash chromatography

| | % area | | | |
|---|---|---|---|---|
| | Impurity at RRT 0.7 | E + Z-isomers | Impurity at RRT 1.08 | RRT 1.12 (Ar—Ar—CH2OH) |
| Before dry flash | 4.6 | 91.3 | <0.5 | 4.1 |
| After dry-flash | 2.5 | 95.6 | <0.5 | 0.7 |

RRT: Relative retention time

The dry-flash chromatography of the crude isomeric mixture does not allow the purification of (3Z,5S)-5-(hydroxymethyl)-1-[(2'-methyl-1,1'-biphenyl-4-yl)carbonyl]pyrrolidin-3-one-O-methyloxime. The E/Z ratio pre and post dry-flash remain in the range of 30/70 to 40/60.

Furthermore, such an approach should be considered on the basis of the scale at which the operation has to be carried out. On a 20 L scale, this operation would not be a time saving approach.

1.3 Assessment Toward Crystalization of the Pure Z from the Crude Isomeric Mixture The first part of the assessment toward crystallisation of the pure formula (3Z,5S)-5-(hydroxymethyl)-1-[(2'-methyl-1,1'-biphenyl-4-yl)carbonyl]pyrrolidin-3-one-O- methyloxime from the crude mixture (3Z,E,5S)-5-(hydroxymethyl)-1-[(2'-methyl-1,1'-biphenyl-4-yl)carbonyl]pyrrolidin-3-one-O-methyloxime, has been looking at solubility and possible crystallisation conditions of the pure (3Z,5S)-5-(hydroxymethyl)-1-[(2'-methyl-1,1'-biphenyl-4-yl)carbonyl]pyrrolidin-3-one-O-methyloxime. The results of the solubility/crystallisation tests carried out on 15 mg scale are reported in Table 2 below

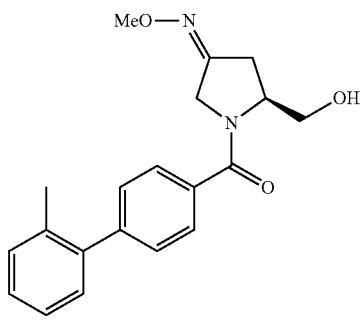

TABLE 2

Qualitative solubility data for (3Z,5S)-5-(hydroxymethyl)-1-
[(2'-methyl-1,1'-biphenyl-4-yl)carbonyl]pyrrolidin-3-
one O-methyloxime

| Solvent | Dissolves in: | Comment |
|---|---|---|
| heptanes | — | insoluble in 20 vol |
| toluene | 2 vol cold | |
| DIPE | 40 vol hot | |
| THF | 4 vol cold | |
| tBuOH | 6 vol hot | |
| MIBK | 4 vol hot | |
| IPA | 4 vol hot | |

The initial solubility screen showed that pure (3Z,5S)-5-(hydroxymethyl)-1-[(2'-methyl-1,1'-biphenyl-4-yl)carbonyl]pyrrolidin-3-one-O-methyloxime isomer is soluble in a range of solvents. On the basis of the above results, crystallisation by addition of anti-solvent was examined and the results reported in Table 3. The anti-solvent was added to a warm solution ca 40-50° C. and allowed to cool to room temperature.

In particular, the water (anti-solvent) was added to a warm (40-50° C.) solution of (3Z,5S)-5-(hydroxymethyl)-1-[(2'-methyl-1,1'-biphenyl-4-yl)carbonyl]pyrrolidin-3-one-O-methyloxime in IPA until cloudiness was reached and the mixture was allowed to cool to room temperature.

TABLE 3

Crystallisation via addition of anti-solvent

| Solvent | Antisolvent | Comment |
|---|---|---|
| toluene 20 vol | heptanes 39 vol | oils out |
| THF 10 vol | heptanes 40 vol | oils out |
| tBuOH 10 vol | water 20 vol | oils out |
| MIBK 10 vol | heptanes 40 vol | oils out |
| IPA 20 vol | water 160 vol | very fine solid, oils out on standing |
| IPA 8 vol | water 18 vol | very fine solid, oils out on standing |
| DMSO 10 vol | water 12 vol | gel |
| NMP 10 vol | water 28 vol | oils out |
| MeOH 10 vol | water 10 vol | oils out |
| DMSO 20 vol | water 16 vol | oils out |
| acetone 10 vol | water 10 vol | oils out |
| DCM 10 vol | heptanes 50 vol | oils out |

The IPA/water crystallisation conditions were applied to a crude isomeric mixture. The toluene solution was first concentrated to dryness prior to dissolution in IPA (8 vol) and addition of water (18 vol). Unfortunately, this resulted in material de-mixing as oil.

In another experiment, the antisolvent was added to a solution of crude (3Z,5S)-5-(hydroxymethyl)-1-[(2'-methyl-1,1'-biphenyl-4-yl)carbonyl]pyrrolidin-3-one-O- methyloxime (90.4% area purity, contained 0.5% w/w toluene and 3.7% w/w THP) at room temperature until cloudiness was reached and the mixture was left to stand at room temperature (Table 4).

TABLE 4

Crystallisation by addition of water at 18-22° C.

| Solvent | Antisolvent | Comment |
|---|---|---|
| MeOH 5 vol | water 3 vol | oils out |
| DMSO 5 vol | water 3 vol | oils out |

At this point of the investigation, no suitable conditions of crystallisation of the pure (3Z,5S)-5-(hydroxymethyl)-1-[(2'-methyl-1,1'-biphenyl-4-yl)carbonyl]pyrrolidin-3-one-O-methyloxime or allowing isolation of solid containing (3Z,5S)-5-(hydroxymethyl)-1-[(2'-methyl-1,1'-biphenyl-4-yl)carbonyl]pyrrolidin-3-one-O-methyloxime have been identified.

Further crystallisation attempts were carried out using crude isomeric mixture of formula (3Z,5S)-5-(hydroxymethyl)-1-[(2'-methyl-1,1'-biphenyl-4-yl)carbonyl]pyrrolidin-3-one-O-methyloxime. In all cases, the volume of solvents was smaller than what used previously and based only on a single solvent. The crude material (E/Z ratio 33:67 and purity (E+Z) 79.52% area) used for this crystallisation was concentrated to a foam (Table 5).

TABLE 5 crystallisation from single solvent at lower volume

| Material | Solvent | Ageing in freezer | Ageing in fridge |
|---|---|---|---|
| 'Pure Z' | Ethyl Acetate 1.8 vol | Crystallises re-dissolves as warms | Stays in solution, with and without seeding after 2 days. |
| Crude | | Does not crystallize with or without seeding. | n/a |
| 'Pure Z' | Diethyl-ether 2.3 vol | On addition of ether at 18-22° C. starts to dissolve then crashes out again. Recovery 70% Used for seeding | n/a |
| Crude | | Oils Re-dissolves as warms | Crystallises recovery 41% E/Z ratio 40/60 purity 85.4% area. (mother liquors E/Z ratio 20/80 purity 62.1% area). Seeds not used. |
| 'Pure Z' | TBME 2.3 vol | Oils Re-dissolves as warms | Stays in solution, with and without seeding after 2 days. |
| Crude | | Oils Re-dissolves as warms | Stays in solution, with and without seeding after 2 days. |

Crystallisation using ethyl acetate followed by aging in a freezer overnight gave crystallisation using the pure formula (3Z,5S)-5-(hydroxymethyl)-1-[(2'-methyl-1,1'-biphenyl-4-yl)carbonyl]pyrrolidin-3-one-O-methyloxime material, but quickly re-dissolved as the sample warmed. No crystals were observed using crude material in ethyl acetate even when seeds were added.

Crystallisation using diethylether followed by aging in a fridge gave crystallisation using the crude (3Z/E,5S)-5-(hydroxymethyl)-1-[(2'-methyl-1,1'-biphenyl-4-yl)carbonyl]pyrrolidin-3-one-O-methyloxime material. The solid was collected in 41% recovery. Unfortunately, the collected solid had a slighter poorer E/Z ratio than the input material and a slightly higher chemical purity, TBME as solvent for both pure Z and crude gave oiling after aging in freezer, and stayed in solution after aging in the fridge with and without seeds.

Suitable crystallization conditions of the crude isomeric mixture allowing improvement of the Z/E ratio and of the purity of the isomeric mixture (E+Z) have not been found.

1.4 Substantially Pure Form of (3Z,5S)-5-(hydroxymethyl)-1-[(2'-methyl-1,1'-biphenyl-4-yl)carbonyl]pyrrolidin-3-one-O-methyloxime

1.4.1 Small Scale Purification

The isolation procedure in substantially pure form of (3Z,5S)-5-(hydroxymethyl)-1-[(2'-methyl-1,1'-biphenyl-4-yl)carbonyl]pyrrolidin-3-one O-methyloxime using a Biotage system (Biotage AB, SE-751 03 Uppsala, Sweden) of the crude isomeric mixture isolated after reduction of the oxime ester (Stage 7 of Example 1).

Five distinct batches (No. 020, 180, 062, 068, 076) of the crude isomeric mixture were purified by Biotage chromatography. Furthermore, different conditions were used regarding batches No. 068 and 076. Purification was performed with a 5% w/w spike of oxime methyl ester added (No. 068), and with an overloaded Biotage column (No. 076).

Each chromatography was run using Biotage 40M cartridges (40 g silica) which had been pre-flushed with toluene. Toluene:MeOH (99:1 v/v) was then eluted and collected in 100 ml fractions (total volume 4 L), followed by a flush of toluene:MeOH (96:4 v/v).

Fractions were analysed by TLC (eluent: ethylaceiate) to determine which fractions could be discarded and which fractions contained Z isomer. These Z fractions were then analyzed by HPLC. The pass criteria for a fraction was >96% Z isomer and <1.2% E isomer.

Surprisingly, the purification through Biotage chromatography of various batches was very efficient as the substantially pure form of (3Z,5S)-5-(hydroxymethyl)-1-[(2'-methyl-1,1'-biphenyl-4-yl)carbonyl]pyrrolidin-3-one O-methyloxime is purified at 99.4% (Batches No. 020, No. 062, No. 068) and at 99.2% (Batches No. 180, No. 076). In particular, the Biotage chromatography in presence of oxime ester removes 5% w/w oxime ester without detriment to recovery or quality (Batch No. 068) and a 25% overcharge of the Biotage column does not cause a decrease in yield or quality (batch No. 076).

TABLE 6 efficiency of the Biotage chromatography

| Batch No. | Input % E/Z | Output % E/Z | yield of Z isomer |
|---|---|---|---|
| 020 | 3.0 g<br>85.7% area purity<br>% E/Z: 30.5/69.5 | Pure Z-fractions:<br>1.0 g<br>98.8% area purity<br>% E/Z: 0.6/99.4 | 33% |
| 180 | 2.0 g<br>92.0% area purity<br>% E/Z: 32.8/67.2 | Pure Z-fractions<br>0.9 g<br>99.6% area purity<br>% E/Z: 0.8/99.2 | 45% |
| 062 | 3.0 g<br>83.5% area purity<br>% E/Z: 32.7/67.3 | Pure Z-fractions<br>1.3 g<br>99.8% area purity<br>% E/Z: 0.6/99.4 | 43% |
|  |  | Mixture:<br>1.2 g<br>91.0% area purity<br>% E/Z: 69.6/30.4 | 11% |
| 068 | 3.0 g spiked with ~5% ester<br>~78% area purity<br>% E/Z: 32.7/67.3 | Pure Z fractions:<br>1.2 g<br>99.8% area purity<br>% E/Z: 0.6/99.4 | 40% |
|  |  | Mixture:<br>0.6 g<br>98.8% area purity<br>% E/Z: 27.9/72.1 | 14% |
| 076 | 3.8 g<br>83.5% area purity<br>% E/Z: 32.7/67.3 | Pure E fractions:<br>1.1 g<br>70.7% area purity<br>% E/Z: 98.7/1.3<br>(19.3% ester) | N/A |
|  |  | Pure Z fractions<br>1.4 g<br>99.8% area purity<br>% E/Z: 0.8/99.2 | 37% |
|  |  | Mixture:<br>1.8 g<br>95.0% area purity<br>% E/Z: 63.6/36.4 | 17% |

1.4.2 Large Scale Purification

Various batches of crude (3Z,5S)-5-(hydroxymethyl)-1-[(2'-methyl-1,1'-biphenyl-4-yl)carbonyl]pyrrolidin-3-one O-methyloxime (0.392 kg, 1.16 mol, 1.0 wt) were charged to a Biotage 150 L SIM unit as an approximate 50% w/w solution in toluene and purified using 1% methanol in toluene (150 L) followed by 2% methanol in toluene (50 L) fraction size 50 L. The collected fractions were analysed by TLC[15] and HPLC analyses, as appropriate. The fractions that were deemed to contain clean (3Z,5S)-5-(hydroxymethyl)-1-[(2'-methyl-1,1'-biphenyl-4-yl)carbonyl]pyrrolidin-3-one-O-methyloxime (criteria; Z-isomer >96.00% area, E-isomer≤1.20% area) were combined and concentrated under vacuum at 40 to 45° C. Absolute ethanol (2×2 L) was added to the residue and the solution concentrated under vacuum at 40 to 45° C. until the foamy solid could be manipulated. The desired product (3Z, 5S)-1-[(biphenyl-4-yl-carbonyl)-5-hydroxy-methyl]pyrrolidine-3-one-O-methyloxime (0.089 Kg, 22.7% w/w, $^1$H NMR (CDCl$_3$) concordant with structure, 99.3% area by HPLC, 98.4:0.9 Z/E ratio was obtained as an off-white to light brown solid.

TABLE 7

Summary of purification of different batches of (3Z,5S)-5-(hydroxymethyl)-1-[(2'-methyl-1,1'-biphenyl-4-yl)carbonyl]pyrrolidin-3-one-O-methyloxime in substantially pure form.

| Batch No. | Input (kg) | Output (kg) | Yield (% w/w) | % Z form (% area) | % E form (% area) |
|---|---|---|---|---|---|
| 12 | 0.392 | 0.089 | 22.8 | 98.65 | 0.85 |
| 116 | 0.392 | 0.114 | 29 | 98.34 | 0.89 |
| 120 | 0.441 | 0.081 | 18.4 | 97.90 | 1.81 |
| 122 | 0.380 | 0.094 | 24.3 | 98.52 | 1.14 |
| 124 | 0.387 | 0.096 | 25.3 | 98.89 | 0.73 |
| 126 | 0.390 | 0.132 | 33.8 | 98.40 | 0.95 |
| 128 | 0.526 | 0.010 | 2 | 98.20 | 0.83 |
| 130 | 0.453 | 0.086 | 19 | 98.46 | 1.23 |
| 132 | 0.440 | 0.082 | 19.3 | 98.86 | 0.85 |
| 134 | 0.39 | 0.144 | 36.9 | 98.73 | 0.96 |
| 138 | 0.273 | 0.098 | 35.9 | 98.92 | 0.66 |
| 140 | 0.463 | 0.059 | 13.1 | 98.52 | 1.13 |
| 142 | 0.462 | 0.084 | 18.4 | 99.37 | 0.48 |
| 144 | 0.442 | 0.126 | 29 | 99.1 | 0.68 |
| 146 | 0.409 | 0.135 | 33.5 | 99.21 | 0.46 |
| 148 | 0.460 | 0.107 | 23.8 | 99.13 | 0.65 |
| 150 | 0.409 | 0.071 | 18 | 98.92 | 0.66 |
| 152 | 0.392 | 0.054 | 14.3 | 98.82 | 0.76 |
| 156 | 0.445 | 0.039 | 8.8 | 98.64 | 0.87 |
| 158 | 0.392 | 0.06 | 15.3 | 98.73 | 0.63 |
| 162 | 0.435 | 0.150 | 34.5 | 98.94 | 0.79 |
| 164 | 0.434 | 0.192 | 44.2 | 99.21 | 0.58 |
| 166 | 0.415 | 0.074 | 17.8 | 98.79 | 0.73 |

TABLE 7-continued

Summary of purification of different batches of (3Z,5S)-5-(hydroxymethyl)-1-[(2'-methyl-1,1'-biphenyl-4-yl)carbonyl]pyrrolidin-3-one-O-methyloxime in substantially pure form.

| Batch No. | Input (kg) | Output (kg) | Yield (% w/w) | % Z form (% area) | % E form (% area) |
|---|---|---|---|---|---|
| 174 | 0.518 | 0.108 | 20.8 | 99.11 | 0.64 |
| 176 | 0.342 | 0.072 | 21 | 98.88 | 0.77 |
| 178 | 0.415 | 0.074 | 17.8 | 99.07 | 0.71 |
| 180 | 0.353 | 0.174 | 49.3 | 99.03 | 0.82 |
| 182 | 0.270 | 0.178 | 65.9 | 99.10 | 0.53 |

Appropriate batches of (3Z,5S)-5-(hydroxymethyl)-1-[(2'-methyl-1,1'-biphenyl-4-yl)carbonyl]pyrrolidin-3-one O-methyloxime (2.713 kg, 1.0 wt) isolated from the Biotage chromatography were combined and dissolved in absolute ethanol (5.16 L, 2.0 vol) at 15 to 25° C., clarified by filtration through glass microfibre paper and an absolute ethanol wash (0.50 L, 0.2 vol) applied to the filter. The combined filtrates were concentrated portion wise under vacuum at 40 to 45° C. The resultant was transferred to drying trays and dried under vacuum at 30° C. for 24 hours. The oven temperature was then increased incrementally from 30 to 40° C. over 80 hours. The level of residual solvent was determined by $^1$H NMR analysis (CDCl$_3$) and when found to be <1.0% w/w the solid was passed through a 500 μm aperture sieve. The solid was returned to the oven and dried at 40 to 42° C. until the solvent level was ≤0.40% w/w to afford (3Z,5S)-1-[(biphenyl-4-yl-carbonyl)-5-hydroxy-methyl]-pyrrolidine-3-O- methyloxime (2.633 Kg, 97.1% w/w, 1H NMR (CDCl$_3$) concordant with structure, 98.65% area by HPLC. The combination procedure is summarized below;

Input: 2.713 kg
Output: 2.633 kg
Yield: 97.1% w/w

Example 2: Capsule Oral formulation 2.1 Bulk Preparation.

Excipients were weighed directly into a beaker, which was transferred into a thermostatic water bath until all excipients were molten at 60° C. Then, always under controlled temperature, small aliquots of (3Z,5S)-5-(hydroxymethyl)-1-[(2'-methyl-1,1'-biphenyl-4-yl)carbonyl]pyrrolidin-3-one O-methyloxime were added until all the drug was dissolved or dispersed, under magnetic stirring, helix mixer or homogenizer.

2.2 Liquid Filling Capsules

The semi-solid bulk was maintained at 60° C. during the liquid filling of the capsule shells. The filling step was performed at 60° C. (both dosing pump and feeder) with an automatic lab-scale capsule-filler machine. The machine was set to the correct dosage by weighing the filled capsules.

Composition of active capsules (Table 8):

TABLE 8

| Component | mg/capsule | |
|---|---|---|
| (3Z,5S) | 30.0 | 300.0 |
| Gelucire 50/13TM | 33.4 | 334.0 |
| LabrasolTM | 16.6 | 166.0 |
| Capsule, gelatine | Size 00 | Size 00 |

Composition of placebo capsules (Table 9):

TABLE 9

| Component | mg/capsule | |
|---|---|---|
| Gelucire 50/13TM | 63.4 | 634.0 |
| LabrasolTM | 16.6 | 166.0 |
| Capsule, gelatine | Size 00 | Size 00 |

Example 3: Granules Oral Formulation

Granules 10% were prepared by hot melt granulation (Table 10):

Hot melt granulation was conducted in a high shear granulator MiMiPro (Procept) using different set-ups depending on the batch size. The general method of manufacture is characterized by the steps of:
i) heat granulator water jacket to melting of waxy binder;
ii) screen powders into the heated bowls and mix gently;
iii) add waxy binder and mix gently; allow wax to soften;
iv) granulate for few minutes; rest the material for few minutes and granulate again if necessary and
v) cool and screen the granules.

In particular, the jacketed vessel was used at 65° C. when Gelucire 50/13 was used as binder. Cover temperature was set at 5° C. lower than the jacketed vessel's. Duration of phases depend on the desired particle size distribution and on the batch size.

TABLE 10

| Component | Amount w/w |
|---|---|
| (3Z,5S) | 10.0% |
| Saccharose | 10.0% |
| Acdisol | 5.0% |
| Gelucire 50/13 | 15.0% |
| Sodium Saccharine | 0.2% |
| Lactose anhydrous | 59.8% |

Hot melt granulation is an alternative technique of granulation: unlike the traditional use of aqueous or organic solvents as binders, in this process the agglomeration is obtained through the addition of a molten binder or a solid binder, which melts during the process and remains as a constituent of the formulation.

Composition of granules 5.8% prepared by spray-drying (Table 11):

The spray-drying process produces porous/hollow particles and amorphous forms of the sprayed material. This approach is used when dissolution rate improvement is required. The spray-drying process consists of four steps: atomisation of feed solution into a spray camera, spray-air contact involving flow and mixing, drying of sprayed droplets at elevated temperatures and separation of dried product from air.

The granules 5.8% were prepared by spray-drying of (3Z,5S), in presence of HP-β-CD (hydroxypropyl-β-cyclodextrin) in hydroethanolic solution. (3Z,5S) is an amorphous material that forms clumps of particles in water, which reduces the drug dissolution rate. Therefore, a hydrophilic excipient, spray-dried together with (3Z,5S) was used to improve the dissolution rate of the drug by preventing the aggregation in water. HP-β-CD was selected as hydrophilic excipients.

HP-β-CD spray dried product was obtained from the hydroalcoholic solution both using the Mini AirPro or Buchi equipment. The feeding solution was prepared by mixing an equal volume of a HP-β-CD (100 g in 200 ml) aqueous solution and an (3Z,5S) (24 g in 200 ml) ethanolic solution that was left for 24 hours under agitation at room temperature. The spray-drying conditions in the fluid bed Mint AirPro were: blower speed 1 m³/min, nozzle pressure 1bar, liquid speed 3, inlet air temperature 70° C.

Spray-dried materials presented very poor flow properties precluding their use for sachet filling. To obtain an easy handling powder, dry granulation and ethanolic wet granulation were the processes applied to the (3Z,5S)-HP-β-CD spray-dried material. The dissolution rate of (3Z,5S) after spray-drying with HP-β-CD was almost instantaneous, in 15 minutes almost all drug was dissolved.

The granulation process by ethanolic wet granulation was performed on the (3Z,5S)-HPβCD spray-dried material. It did not modify the dissolution rate of the drug when compared to the (3Z,5S)-HPβCD spray-dried material.

It produced a material that showed almost instantaneous dissolution of the drug (Table 11).

TABLE 11

| Component | Amount w/w |
|---|---|
| (3Z,5S) | 5.8% |
| Saccharose | 10.0% |
| Acdisol | 3.0% |
| Sodium saccharine | 0.2% |
| HP-β-CD | 24.2% |
| Poloxamer 188 | 2.0% |
| Avicel RC 591 | 10.0% |
| Avicel PH 112 | 10.0% |
| Lactose monohydrate | 34.8% |

Example 4: Conventional Tablet Oral Formulation

A solution containing (3Z,5S) dissolved in Labrasol:Ethanol 3:1 v/v was prepared by heating at 45° C. and adding stepwise the required amount of drug, Zeopharm 600 was dried for 2 hours into a vacuum oven at 50° C. The addition of the solution on Zeopharm 600 bed was carried out into a 1900 ml bowl at 5 ml/mm. The granulator was set as follows: impeller at 900 rpm, chopper at 3500 rpm, and cover temperature at 80° C. To remove most of the solvent, the material was left overnight at room temperature, and 3.5 hours in a vacuum oven at 50° C. As the granule-adsorbate particle size was slightly high, the material was sieve-milled first through a 1.5 mm sieve and then through a 1 mm sieve. The production yield, including the milling step, was 89.68%. The granule-adsorbate (87.5%) was then mixed with AcDiSol (4%), Compritol 888 ATO (3.5%), GL100 (0.2%) and Zeopharm 600 (4.8%) for 20 minutes at 22 r.p.m in the Turbula mixer. The final blend for tabletting possessed a good (3Z,5S) content uniformity. The conventional tablets were produced by compression of the granules using the eccentric tabletting machine EK-0.

Conventional tablets of the compound of formula (3Z,5S)-5-[(hydroxymethyl)-1-[(2'-methyl-1,1'-biphenyl-4-yl)carbonyl]pyrrolidin-3-one O-methyloxime, and/or an active metabolite thereof, were prepared using carriers of calcium silicate (Table 12).

TABLE 12

| Component | Amount w/w |
|---|---|
| (3Z,5S) | 35% |
| Acdisol | 4% |

TABLE 12-continued

| Component | Amount w/w |
|---|---|
| Calcium silicate (Zeopharm 600) | 32.7% |
| Compritol ATO 888 | 3.5% |
| Labrasol | 24.6% |
| Rx GL 100 | 0.2% |

Example 5: Dispersible Tablet Oral Formulation

A 850 g batch granulate was produced and then compressed into tablets. A 5000 ml vessel set-up was used for this preparation. Calcium silicate was vacuum dried prior to use. The wet granulation was conducted with (3Z,5S)-5-(hydroxymethyl)-1-[(2'-methyl-1,1'-biphenyl-4-yl)carbonyl]pyrrolidin-3-one O-methyloxime and all excipients (with the exception of the lubricant) in a high shear granulator at room temperature with only the cover of the granulator heated (65° C.).

In the granulation process after a gentle pro-mix phase, an alternation of liquid addition and mixing phases of few minutes duration was set-up.

A total amount of 80 ml of ethanol was necessary to obtain suitable granules. A final milling and/or sieving step was necessary to obtain a better granule size distribution. The resulting granules were blended with the lubricant before compression.

A single punch eccentric tabletting machine was used.

The compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, is in the form of dispersible tablets containing 50 or 200 mg of active drug substance (Table 13).

TABLE 13

| Component | Amount mg | Amount mg | % (w/w) | Function |
|---|---|---|---|---|
| (3Z,5S) | 50.0 | 200.00 | 20.0 | Active drug substance |
| Calcium silicate | 12.5 | 50.0 | 5.0 | Carrier |
| PVP 30K | 2.5 | 10.0 | 1.0 | Binder |
| Poloxamer 188 | 5.0 | 20.0 | 2.0 | Wetting agent |
| Sodium croscarmellose | 12.5 | 50.0 | 5.0 | Disintegrant |
| Microcrystalline cellulose 112 | 37.5 | 150.0 | 15.0 | Diluent |
| Lactose monohydrate | 119.5 | 478.0 | 47.8 | Diluent |
| Sodium saccharine | 0.5 | 2.0 | 0.2 | Sweetener |
| Glycerol dibehenate | 10.0 | 40.0 | 4.0 | Lubricant |
| Total | 250.0 | 1000.0 | — | |

Example 6: Dimensions of the Tablets

For example, the shape and dimensions of the tablets are the following;

TABLE 14

| Tablet or dispersible tablet | Shape and dimensions |
|---|---|
| 50 mg | Capsule shape; 14 × 6 mm or 13 × 6 mm |
| 200 mg | Capsule shape; 22 × 9 mm or 19 × 9 mm |

Example 7: Pharmacokinetics Studies in the Dog

A pharmacokinetic study was conducted to measure the plasma concentration of the compound of formula (3Z,5S)-5-(hydroxymethyl)-1-[(2'-methyl-1,1'-biphenyl-4-yl)carbonyl]pyrrolidin-3-one O-methyloxime following oral administration of said compound to female Beagle dogs. Following the protocol (Table 15), 5 dogs were administered with an oral formulation composed of liquid filled capsules ("Reference capsule"), 5 dogs were administered with an oral formulation composed of granules 10% (formulation 1), 5 dogs were administered with an oral formulation composed of granules 5.8% (formulation 2), 5 dogs were administered with a dispersible tablet (formulation 3), 5 dogs were administered with a conventional tablet (formulation 4). Also 5 dogs were administered by the IV route of administration ("Reference IV") a solution of the compound of formula (3Z,5S)-5-(hydroxymethyl)-1-[(2'-methyl-1,1'-biphenyl-4-yl)carbonyl]pyrrolidin-3-one O-methyloxime at 15 mg/kg. Blood sampling was performed at 0, 0.25, 0.5, 1, 2, 4, 6, 8, 24, 48 and 72 h.

Figure 3:
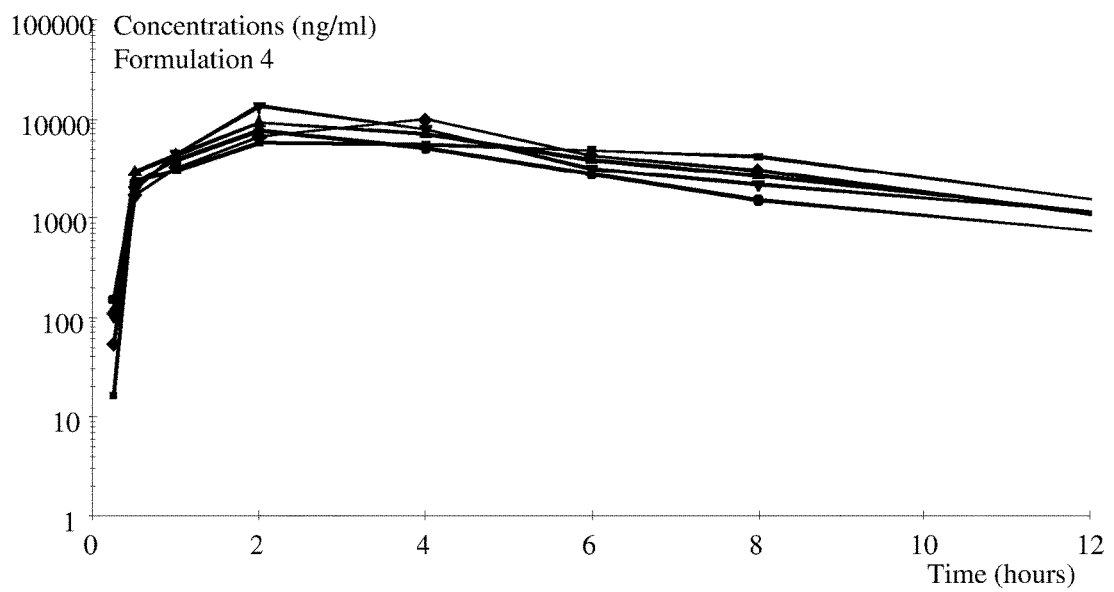
FIG. 3: Individual plasma concentration profiles of formulation 4 (conventional tablets) in the dog. Plasma concentration of the compound of formula (3Z,5S) is measured (ng/ml) for each dog (n=5) for the time period from 0 to 12 h.

Individual plasma profile for each dog are presented on FIG. 2 (formulation 3), and FIG. 3 (formulation 4) to show the inter-animal variability.

7.2 Pharmacokinetic Parameters of Solid Oral Formulations in the Dog

In pharmacokinetics, the bioavailability is measured by calculating the area under the curve (AUC) of the product concentration vs. time profile. The absolute bioavailability compares the bioavailability of the product in systemic circulation following oral administration with the bioavailability of the product following intravenous administration.

"D" as used herein refers to the dose that is the amount of drug administered.

"Cmax" as used herein refers to the peak plasma concentration of a drug after administration wherein the concentration is the amount of drug in a given volume of plasma.

"Tmax" as used herein refers to the time to reach Cmax.

"$T_{1/2}$" as used herein refers to the elimination half-life as the time required for the concentration of the drug to reach half of its original value.

TABLE 15

| Group | Reference IV | Reference capsule | Formulation 1 | Formulation 2 | Formulation 3 | Formulation 4 |
|---|---|---|---|---|---|---|
| Formulation | Solution of (3Z, 5S) | Liquid filled capsules | Granules 10% | Granules 5.8% | Dispersible tablet 200 mg | Conventional tablet 200 mg |
| Dose mg/kg | 15 mg/kg | 300 mg/dog | 20 | 20 | 23.4 (3.4) (200 mg/dog) | 23.3 (3.2) (200 mg/dog) |
| Volume of administration | | 1 capsule size 00 | 5 ml/kg | 5 ml/kg | 50 ml/dog | 50 ml/dog |

7.1 Plasma Concentration Profiles of Solid Oral Formulations in the Dog

FIG. 1A shows the plasma concentration vs. time profile of the different formulations over the time period from 0 to 72 h. FIG. 1B shows an enlargement of FIG. 1A for the time period from 0 to 12 h. The curve corresponding to formulation 3 (dispersible tablet) shows that the maximum concentration of the active substance is detected rapidly at about 0.5-1 hour following its administration. In comparison, the maximum concentration of the active substance is detected at about 2-4 hours following administration of formulation 4 (conventional tablet).

"AUC" as used herein refers to the area under the curve that is the integral of the concentration-time curve (after a single dose or in steady state).

"F %;" as used herein refers to the bioavailability that is the systemically available fraction of a drug. The index of bioavailability after oral administration is calculated by the following equation using the AUC found after i.v. administration:

$$F\% = (AUC_{OS}/AUC_{IV}) \times (Dose_{IV}/Dose_{OS}) \times 100$$

TABLE 16

| | Numbers in brackets represent the standard deviation | | | | | |
|---|---|---|---|---|---|---|
| Group | Reference IV | Reference Capsule | 1 | 2 | 3 | 4 |
| Formulation | IV | Capsule | Granules 10% | Granules 5.8% | Dispersible tablet | Conventional tablet |
| Route of administration | IV | OS | OS | OS | OS | OS |
| Dose (mg/kg) | 15 | 34.4 (±4.0) | 20 | 20 | 25.7 (±2.3) | 23.3 (±3.2) |
| C (0.25 h) (ng/ml) | — | 13 (±15) | 3590 (±1450) | 4523 (±2757) | 5108 (±1955) | 88 (±54) |
| Cmax (ng/ml) | 17071 (±6162) | 15243 (±3194) | 7488 (±2236) | 8722 (±2036) | 13966 (±3217) | 9245 (±2869) |
| Tmax (h) | — | 4 (4-4) | 1 (0.5-2) | 0.5 (0.5-0.5) | 1 (0.5-1) | 2 (2-4) |
| AUC (h*ng/ml) | 38684 (±2310) | 80139 (±18793) | 32775 (±9120) | 29893 (±7483) | 58952 (±5770) | 53563 (±7570) |
| T1/2 (h) | 9.5 (±4.4) | 7.1 (±1.2) | 5.9 (±3.9) | 4.7 (±0.9) | 6.6 (±0.6) | 5.0 (±1.7) |

TABLE 16-continued

Numbers in brackets represent the standard deviation

| Group | Reference IV | Reference Capsule | 1 | 2 | 3 | 4 |
|---|---|---|---|---|---|---|
| F (%) | — | 90 (±15) | 64 (±18) | 58 (±15) | 89 (±9) | 89 (±13) |

Formulations 1 and 2 (granules) showed equivalent responses and were characterized by a favorable fast compound absorption (Table 16), Their absolute bioavailability was good (about 60%), even though lower than the other formulations tested, but associated with a moderate variability between animals. Dispersible tablets Formulation 3 showed a rate of absorption comparable to granules Followed by a decay comparable to the Reference Capsule formulation. A very high compound exposure highlighted by the absolute bioavailability (higher than after administration of granules and comparable to the liquid filled capsule reference formulation) was observed. Conventional tablets Formulation 4 gave a delayed absorption compared to Formulation 3 with a roughly similar bioavailability.

Formulation 3 appears overall the most suitable tor the indication of preterm labor. By comparison with the Reference Capsule formulation (300 mg/dog, liquid filled capsules), the results highlight a faster compound absorption (about 37% of the amount found at Cmax already found at the first sampling time, 0.25 h), Cmax reached at earlier time (median Tmax=1 h), terminal elimination rate comparable ($T_{1/2}$ of about 7 h) and overall more uniform responses between animals. Formulation 3 exposure was equivalent to the Reference Capsule formulation and also absolute bioavailability was equivalent to that of the Reference Capsule formulation (89% vs. 90%).

7.3 Individual Plasma Concentration Profiles of Formulation 3 in the Dog

Route of administration: Oral

Administered dose of (3Z,5S): 200 mg/dog

Formulation 3: 200 mg dispersible tablet

Dose regimen: Single

TABLE 17

| Sampling time (h) | Animal No. (3Z,5S) plasma concentrations in ng/mL | | | | |
|---|---|---|---|---|---|
|  | 6F | 7F | 8F | 9F | 10F |
| 0 (pre-dose) | 1.5 | 2.3 | * | 3.4 | * |
| 0.25 | 8122 | 3965 | 2937 | 4994 | 5522 |
| 0.5 | 14107 | 9206 | 6913 | 16555 | 9070 |
| 1 | 18285 | 11934 | 11575 | 9137 | 11479 |
| 2 | 8175 | 7289 | 8341 | 7476 | 7942 |
| 4 | 5151 | 5188 | 6589 | 5660 | 4924 |
| 6 | 2508 | 2807 | 3434 | 2849 | 3027 |
| 8 | 1343 | 1626 | 2456 | 1819 | 3389 |
| 24 | 70 | 166 | 422 | 355 | 36 |
| 48 | 5 | 8.7 | 12 | 22 | 12 |
| 72 | 3.7 | 2 | 2.1 | 2.3 | 3.4 |

* = Below the lower limit of quantification (1 ng/mL)

Remarkably, at 0.5 hour time point following administration of the dispersible tablet, the concentration in blood of the compound of formula (3Z,5S) is comprised between 59% to 100% of Cmax indicating that said formulation is suitable for providing a rapid onset of action (Table 17).

7.4 Individual Pharmacokinetic Parameters of Formulation 3 in the Dog

TABLE 18

| PK parameter | Animal No. | | | | |
|---|---|---|---|---|---|
|  | 6F | 7F | 8F | 9F | 10F |
| Cmax (ng/ml) | 18285 | 11934 | 11575 | 16555 | 11479 |
| Tmax (h) | 1 | 1 | 1 | 0.5 | 1 |
| C (0.25 h) (ng/ml) | 8122 | 3965 | 2937 | 4994 | 5522 |
| AUC (h * ng/ml) | 56242 | 52929 | 67865 | 61111 | 56615 |
| $T_{1/2}$ (h) | 6 | 5.8 | 5.7 | 6.6 | 7.2 |
| F (%) | 85 | 80 | 102 | 92 | 85 |

The maximum concentration in blood of the compound of formula (3Z,5S) is reached at a time Tmax between 0.5 to 1 hour following administration of Formulation 3 (dispersible tablet). In addition, Formulation 3 is characterized by a bioavailability of the compound of formula (3Z,5S) comprised between 80-100% (fable 18).

7.5 Individual Plasma Concentration Profiles of Formulation 4 in the Dog

TABLE 19

| Sampling time (h) | Animal No. (3Z,5S) plasma concentrations in ng/mL | | | | |
|---|---|---|---|---|---|
|  | 1F | 2F | 3F | 4F | 5F |
| 0 (pre-dose) | * | * | * | * | * |
| 0.25 | 152 | 17 | 53 | 116 | 104 |
| 0.5 | 2217 | 2379 | 1680 | 2926 | 1945 |
| 1 | 3907 | 3031 | 3241 | 4339 | 4482 |
| 2 | 7759 | 5761 | 6671 | 9227 | 13492 |
| 4 | 5171 | 5646 | 9983 | 7085 | 7848 |
| 6 | 2806 | 4822 | 4307 | 3856 | 3185 |
| 8 | 1527 | 4195 | 3051 | 2713 | 2211 |
| 24 | 87 | 78 | 53 | 92 | 172 |
| 48 | 1.8 | 3.1 | 1.9 | 4.5 | 4.5 |
| 72 | * | * | * | 1.2 | 1.6 |

* = Below the lower limit of quantification (1 ng/mL)

The maximum concentration in blood of the compound of formula (3Z,5S) is reached at a time Tmax between 2 to 4 hours following administration of Formulation 4 (conventional tablet).

At 0.5 hour time point following administration of Formulation 4 (conventional tablet), the concentration in blood of the compound of formula (3Z,5S) is comprised between 14% to 41% of Cmax (Table 19) a value markedly lower than for formulation 3 which is characterized by a higher concentration of the compound of formula (3Z,5S) comprised between 59% to 100% of Cmax (Table 17).

7.6 Individual Pharmacokinetic Parameters of Formulation 2 in the Dog

TABLE 20

| PK parameter | Animal No. | | | | |
|---|---|---|---|---|---|
| | 11F | 12F | 13F | 14F | 15F |
| Cmax (ng/ml) | 7029 | 9050 | 9897 | 6347 | 11287 |
| Tmax (h) | 0.5 | 0.5 | 0.5 | 0.5 | 0.5 |
| C (0.25 h) (ng/ml) | 3521 | 1275 | 4512 | 4445 | 8865 |
| AUC (h · ng/ml) | 21062 | 34881 | 39126 | 23931 | 30466 |
| $T_{1/2}$ (h) | 3.3 | 5.3 | 4.5 | 5.1 | 5.4 |
| F (%) | 41 | 68 | 76 | 46 | 59 |

Formulation 2 (granule 5.8%) is characterized by a bioavailability of the compound of formula (3Z,5S) comprised between 41-76% (Table 20) markedly lower than for formulation 3 which is characterized by a very high bioavailability comprised between 80-100% (Table 18).

Thus, the dispersible tablet formulation 3 displays characteristics that are suitable for providing a last onset of action and high bioavailability for the treatment of preterm labor. In contrast conventional tablet (formulation 4) or granules (formulation 2) do not meet the pharmacokinetic requirements for treating preterm labor.

Example 8: Pharmacokinetics Studies in Human

Study Protocol

Twelve healthy Caucasian women aged 54-62 years (mean 58.3 years), with a weight of 51 to 67 kg (mean 60.6 kgs±5.1) and a body mass index ranging between 19.4-25.5 kg/m2 (mean 23.12 kg/m2±2.05) were enrolled. They were administered, on three separate treatment periods of one week, either two consecutive (3Z,5S) doses of 600 mg/day (administered to subjects using 3 dispersible tablets of 200 mg in 150 ml of water) or two intramuscular injections of 12 mg/day betamethasone or both drugs in combination.

Betamethasone (Célestene®, Schering-Plough, France) was administered by intramuscular injection of 12 mg/3 ml into the gluteus muscle, which is a recommended dose for antenatal betamethasone in preterm labor for the prevention of respiratory distress syndrome in neonates.

One subject (Subject S6) was withdrawn from the study after the first treatment period, due to high pre-dose blood pressure in the second treatment period. Therefore, pharmacokinetic parameters of the treatment with (3Z,5S) dispersible tablets were calculated for 12 subjects, whereas pharmacokinetic parameters of the combination treatment were assessed for 11 participants.

During each treatment period of one week, blood samples were collected for the analysis of (3Z,5S) and betamethasone at time points 0 (pre-dose) and at 0.25, 0.5, 0.75, 1, 1.5, 2, 3, 4, 6, 8, 10, 12, 16, 20 and 24 hours after first dose on day 1. The plasma was prepared and stored below –20° C. All samples were analysed using validated LC-MS/MS methods. For the analysis of (3Z,5S), the lower limit of quantification was 1.0 ng/mf. For betamethasone analyses, the lower limit of quantification was 0.5 ng/ml.

Pharmacokinetic parameters were estimated by non-compartmental methods using the Phoenix® WinNonLin® version 6.3 (Pharsight). The following pharmacokinetic parameters were calculated for (3Z,5S) during each treatment period: measured maximum concentration (Cmax), time to Cmax (Tmax), and area under the plasma concentration-time curve (AUC).

8.1 Individual Plasma Concentration Profiles of (3Z,5S) Dispersible Tablet (Formulation 3) in Human Tables 21 to 23 show plasma concentration profiles of (3Z,5S) and pharmacokinetic parameters concerning (3Z,5S) which was administered to subjects using 3 dispersible tablets of 200 mg in 150 ml of water.

TABLE 21

| | Subject S Plasma concentration of (3Z, 5S) in ng/ml | | | | | | | | | | | |
|---|---|---|---|---|---|---|---|---|---|---|---|---|
| Time | S1 | S2 | S3 | S4 | S5 | S6 | S7 | S8 | S9 | S10 | S11 | S12 |
| 0.25 | 1190 | 270 | 335 | 867 | 574 | 234 | 481 | 407 | 1730 | 1610 | 409 | 1990 |
| 0.5 | 3020 | 1170 | 1310 | 3120 | 2020 | 860 | 1550 | 1510 | 2630 | 2640 | 2510 | 2690 |
| 0.75 | 3010 | 1450 | 1810 | 2760 | 2220 | 1400 | 2090 | 1440 | 2700 | 2120 | 2350 | 3070 |
| 1 | 3100 | 2410 | 1810 | 3160 | 1830 | 1560 | 1440 | 1450 | 2670 | 2180 | 1940 | 2900 |
| 1.5 | 3280 | 3380 | 1650 | 4070 | 1600 | 1770 | 1790 | 1370 | 2570 | 3190 | 2990 | 3600 |
| 2 | 3170 | 3150 | 1520 | 3820 | 1550 | 1940 | 2440 | 2100 | 3050 | 2980 | 4100 | 3630 |
| 3 | 3060 | 3360 | 1540 | 3070 | 1560 | 2060 | 2280 | 2060 | 2660 | 2980 | 3410 | 3570 |
| 4 | 2870 | 2600 | 2300 | 2940 | 1990 | 3060 | 2290 | 2160 | 2730 | 2770 | 3300 | 3460 |
| 6 | 2400 | 2200 | 1910 | 1910 | 1580 | 2000 | 1800 | 1670 | 2280 | 1780 | 1960 | 1980 |
| 8 | 1710 | 1870 | 1800 | 1940 | 1310 | 1670 | 1560 | 1290 | 1690 | 155 | 1620 | 1760 |
| 12 | 1420 | 1870 | 1720 | 1630 | 949 | 1380 | 1250 | 794 | 1510 | 1400 | 1650 | 1410 |
| 16 | 1000 | 1040 | 1030 | 1170 | 640 | 981 | 762 | 586 | 928 | 844 | 1020 | 866 |
| 20 | 804 | 868 | 718 | 978 | 554 | 812 | 654 | 444 | 698 | 818 | 827 | 699 |
| 24 | 765 | 680 | 567 | 843 | 385 | 792 | 501 | 327 | 555 | 560 | 759 | 612 |

TABLE 22

| | Subject S % of Cmax | | | | | | | | | | | |
|---|---|---|---|---|---|---|---|---|---|---|---|---|
| Time | S1 | S2 | S3 | S4 | S5 | S6 | S7 | S8 | S9 | S10 | S11 | S12 |
| 0.25 | 36% | 8% | 15% | 21% | 26% | 8% | 20% | 19% | 57% | 50% | 10% | 55% |
| 0.5 | 92% | 35% | 57% | 77% | 91% | 28% | 64% | 70% | 86% | 83% | 61% | 74% |
| 0.75 | 92% | 43% | 79% | 68% | 100% | 46% | 86% | 67% | 89% | 66% | 57% | 85% |
| 1 | 95% | 71% | 79% | 78% | 82% | 51% | 59% | 67% | 88% | 68% | 47% | 80% |
| 1.5 | 100% | 100% | 72% | 100% | 72% | 58% | 73% | 63% | 84% | 100% | 73% | 99% |
| 2 | 97% | 93% | 66% | 94% | 70% | 63% | 100% | 97% | 100% | 93% | 100% | 100% |

TABLE 22-continued

| | Subject S % of Cmax | | | | | | | | | | | |
|---|---|---|---|---|---|---|---|---|---|---|---|---|
| Time | S1 | S2 | S3 | S4 | S5 | S6 | S7 | S8 | S9 | S10 | S11 | S12 |
| 3 | 93% | 99% | 67% | 75% | 70% | 67% | 93% | 95% | 87% | 93% | 83% | 98% |
| 4 | 88% | 77% | 100% | 72% | 90% | 100% | 94% | 100% | 90% | 87% | 80% | 95% |
| 6 | 73% | 65% | 83% | 47% | 71% | 65% | 74% | 77% | 75% | 56% | 48% | 55% |
| 8 | 52% | 55% | 78% | 48% | 59% | 55% | 64% | 60% | 55% | 49% | 40% | 48% |
| 10 | 46% | 50% | 70% | 38% | 51% | 49% | 56% | 45% | 51% | 45% | 36% | 41% |
| 12 | 43% | 55% | 75% | 40% | 43% | 45% | 51% | 37% | 50% | 44% | 40% | 39% |
| 16 | 30% | 31% | 45% | 29% | 29% | 32% | 31% | 27% | 30% | 26% | 25% | 24% |
| 20 | 25% | 26% | 31% | 24% | 25% | 27% | 27% | 21% | 23% | 26% | 20% | 19% |
| 24 | 23% | 20% | 25% | 21% | 17% | 26% | 21% | 15% | 18% | 18% | 19% | 17% |

Following administration of the dispersible tablet of the invention, the maximum concentration Cmax in blood of the compound of formula (3Z,5S) is reached at a time Tmax between 0.5 to 4 hours. In particular, Tmax is in the range of 0.5 to 2 hours for 9 subjects, and in the range of 0.5 to 1.5 hours for 5 subjects.

Of note, at 0.5 hour time point, the concentration in blood of the compound of formula (3Z,5S) is comprised between 55% to 95% of Cmax for 10 subjects, preferentially between 57% to 92% of Cmax, indicating that the solid oral formulation is rapidly absorbed and suitable for providing a rapid onset of pharmacological action. For subjects S2 and S6, the plasma concentration of (3Z,5S) was below 55% at 0.5 h, respectively 35% and 28% of Cmax. However, it was respectively 71% and 51% of Cmax at 1 h following administration of the dispersible tablet which concentration is suitable for the management of preterm labor.

8.2 Individual Pharmacokinetic Parameters of (3Z,5S) Dispersible Tablet (Formulation 3) in Human

TABLE 23

| | Subject S | | | | | | | | | | | |
|---|---|---|---|---|---|---|---|---|---|---|---|---|
| | S1 | S2 | S3 | S4 | S5 | S6 | S7 | S8 | S9 | S10 | S11 | S12 |
| Cmax ng/ml | 3280 | 3380 | 2300 | 4070 | 2220 | 3060 | 2440 | 2160 | 3050 | 3190 | 4100 | 3630 |
| Tmax hour | 1.5 | 1.5 | 4 | 1.5 | 0.75 | 4 | 2 | 4 | 2 | 1.5 | 2 | 2 |
| AUC ng.h/ml | 38557 | 39042 | 32421 | 41209 | 24814 | 33388 | 29867 | 24085 | 36317 | 34853 | 38944 | 38467 |

8.3 Plasma Concentration Profiles in Human for a Combination of (3Z,5S) and Betamethasone Tables 24 to 26 show plasma concentration profiles of (3Z,5S) and pharmacokinetic parameters concerning (3Z,5S) administered in combination with Betamethasone,

TABLE 24

Plasma concentration of (3Z, 5S) in ng/ml

| | Subject S Plasma concentration of (3Z, 5S) in ng/ml | | | | | | | | | | |
|---|---|---|---|---|---|---|---|---|---|---|---|
| Time | S1 | S2 | S3 | S4 | S5 | S7 | S8 | S9 | S10 | S11 | S12 |
| 0.25 | 41.8 | 597 | 322 | 486 | 264 | 536 | 359 | 396 | 1150 | 934 | 934 |
| 0.5 | 210 | 3240 | 978 | 1890 | 1250 | 2510 | 1100 | 2420 | 2590 | 2040 | 1980 |
| 0.75 | 407 | 5290 | 1130 | 2210 | 1780 | 2910 | 1610 | 2570 | 2490 | 2060 | 3010 |
| 1 | 593 | 5320 | 1100 | 2290 | 1580 | 2600 | 1730 | 2250 | 2350 | 1930 | 3020 |
| 1.5 | 1050 | 4940 | 1350 | 3550 | 2010 | 2620 | 1860 | 2300 | 3130 | 1920 | 3430 |
| 2 | 1050 | 4750 | 2180 | 4230 | 2080 | 3290 | 2400 | 2270 | 3520 | 4170 | 3550 |
| 3 | 1480 | 4480 | 3500 | 3620 | 2280 | 3540 | 2520 | 2340 | 3150 | 4440 | 3780 |
| 4 | 2040 | 4130 | 3500 | 3880 | 2350 | 3430 | 2540 | 2310 | 3340 | 4020 | 3550 |
| 6 | 1440 | 2510 | 1710 | 2290 | 2050 | 2710 | 1600 | 2910 | 2350 | 2690 | 2670 |
| 8 | 1470 | 1950 | 1530 | 2180 | 1680 | 2180 | 1250 | 2280 | 1820 | 2300 | 1970 |
| 10 | 1570 | 2090 | 1250 | 2120 | 1270 | 1960 | 981 | 2120 | 1620 | 1840 | 1750 |
| 12 | 1300 | 1870 | 1430 | 1930 | 1040 | 1750 | 1000 | 1970 | 1430 | 1630 | 2130 |
| 16 | 521 | 1140 | 1000 | 1330 | 693 | 935 | 550 | 959 | 869 | 951 | 1010 |
| 20 | 512 | 1100 | 943 | 1240 | 481 | 831 | 471 | 825 | 746 | 786 | 877 |
| 24 | 418 | 8285 | 712 | 1020 | 353 | 569 | 383 | 605 | 533 | 650 | 657 |

TABLE 25

% of Cmax

Subject S % of Cmax

| Time | S1 | S2 | S3 | S4 | S5 | S7 | S8 | S9 | S10 | S11 | S12 |
|---|---|---|---|---|---|---|---|---|---|---|---|
| 0.25 | 2% | 11% | 9% | 11% | 11% | 15% | 14% | 14% | 33% | 21% | 25% |
| 0.5 | 10% | 61% | 28% | 45% | 53% | 71% | 43% | 83% | 74% | 46% | 52% |
| 0.75 | 20% | 99% | 32% | 52% | 76% | 82% | 63% | 88% | 71% | 46% | 80% |
| 1 | 29% | 100% | 31% | 54% | 67% | 73% | 68% | 77% | 67% | 43% | 80% |
| 1.5 | 51% | 93% | 39% | 84% | 86% | 74% | 73% | 79% | 89% | 43% | 91% |
| 2 | 51% | 89% | 62% | 100% | 89% | 93% | 94% | 78% | 100% | 94% | 94% |
| 3 | 73% | 84% | 100% | 86% | 97% | 100% | 99% | 80% | 89% | 100% | 100% |
| 4 | 100% | 78% | 100% | 92% | 100% | 97% | 100% | 79% | 95% | 91% | 94% |
| 6 | 71% | 47% | 49% | 54% | 87% | 77% | 63% | 100% | 67% | 61% | 71% |
| 8 | 72% | 37% | 44% | 52% | 71% | 62% | 49% | 78% | 52% | 52% | 52% |
| 10 | 77% | 39% | 36% | 50% | 54% | 55% | 39% | 73% | 46% | 41% | 46% |
| 12 | 64% | 35% | 41% | 46% | 44% | 49% | 39% | 68% | 41% | 37% | 56% |
| 16 | 26% | 21% | 29% | 31% | 29% | 26% | 22% | 33% | 25% | 21% | 27% |
| 20 | 25% | 21% | 27% | 29% | 20% | 23% | 19% | 28% | 21% | 18% | 23% |
| 24 | 20% | 16% | 20% | 24% | 15% | 16% | 15% | 21% | 15% | 15% | 17% |

Following administration of the combination (3Z,5S) dispersible tablet and betamethasone, the maximum concentration Cmax in blood of the compound of formula (3Z,5S) is reached at a time Tmax between 1 to 6 hours. In particular, Tmax is in the range of 2 to 4 hours for 9 subjects, and in the range of 2 to 3 hours for 6 subjects.

At 0.5 hour time point, the concentration in blood of the compound of formula (3Z,5S) is comprised between 43% to 83% of Cmax for 10 subjects indicating that the solid oral formulation administered in combination with betamethasone is rapidly absorbed and suitable for providing a rapid onset of pharmacological action. For subjects S1 and S3, the plasma
concentration of (3Z,5S) was below 43% at 0.5 h, respectively 10% and 28% of Cmax. However, it was respectively 51% and 62% of Cmax at 2 h following administration of the dispersible tablet.

8.3 Pharmacokinetic Parameters in Human for a Combination of (3Z,5S) Formulation 3 and Betamethasone

TABLE 26

| Subject S | S1 | S2 | S3 | S4 | S5 | S7 | S8 | S9 | S10 | S11 | S12 |
|---|---|---|---|---|---|---|---|---|---|---|---|
| Cmax ng/ml | 2040 | 5320 | 3500 | 4230 | 2350 | 3540 | 2540 | 2910 | 3520 | 4440 | 3780 |
| Tmax hour | 4 | 1 | 3 | 2 | 4.03 | 3 | 4 | 6 | 2 | 3 | 3 |
| AUC ng.h/ml | 24060 | 50306 | 34518 | 47627 | 28322 | 42044 | 25974 | 39688 | 38208 | 43314 | 44082 |

Example 9: The Manufacturing Process of Dispersible Tablets

The manufacturing process of the dispersible tablets of the present invention comprises the following steps:

(i) Preparing a mixture consisting of 20% of (3Z,5S)-5-(hydroxymethyl)-1-[(2'-methyl-1,1'-biphenyl-4-yl)carbonyl]pyrrolidin-3-one-O-methyloxime, 5% of calcium silicate, 1% of PVP 30K, 2% of Poloxamer 188, 5% of sodium croscarmellose, 15% of Microcrystalline cellulose 112, 47.8% of lactose monohydrate, 0.2% sodium saccharine, in weight based on the total weight of the tablet;

(ii) Wet granulating in presence of ethanol and vacuum drying;

(iii) Sieving the granules; (iv) Blending the granules with 4% of glycerol dibehenate in weight based on the total weight of the tablet;

(v) Tabletting.

The wet granulation is preferably conducted in a high shear granulator at room temperature with a minimal amount of ethanol equivalent to at least 7.4% (in weight based on the total weight of the tablet). The vacuum drying is performed at room temperature A sieving step is applied on the resulting granules. Sieved glycerol dibehenate is blended with the granules. The final blend is compressed with an eccentric or rotary tablet press and adapted punches for the targeted dispersible tablet strength.

Example 10: Stability Study of Dispersible Tablet (Formulation 3)

The determination of the (3Z,5S) content after dissolution of dispersible tablets is performed by HPLC using the following parameters:
Apparatus: USPII paddle apparatus
Dissolution medium: 0.5% Sodium Lauryl Sulfate in water
Dissolution medium volume: 900 ml
Dissolution medium temperature: 37° C.+/−0.5° C.
Rotation speed, 50 rpm
Sampling time: 15, 30, 45, 60 and 120 min
Sampling volume: 3 ml Separative technique; PALL Acrodisc PSF GxP/Glass 1.0 µm The paddle assembly is arranged so that the bottom of the paddle was 2.5 cm±0.2 cm from the inside bottom of the flask. The appropriate volume of dissolution medium is poured into each one of the six dissolution vessels. The medium is equilibrated at 37.0 C±0.5 C. A (3Z,5S) dispersible tablet is inserted into each vessel. The paddles rotation was controlled at 50 rpm. At the designated time-points, 3 ml of medium is taken from a zone midway between the surface of the dissolution medium and the top of the blade of the paddle. Then, the sample is filtered through a PALL Acrodisc PSF GxF/Glass 1.0 µm directly info an HPLC vial for analysis.

Stability data are available at 1, 2 and 6 months storage time for (3Z,5S) dispersible tablets packaged in Alu/Alu blister packs. Parameters such as tablet appearance, (3Z,5S) content in % compared to the initial content value, disintegration time and dissolution were assessed (Tables 28 and 29).

The initial concentration value of (3Z,5S) measured by HPLC with a dispersible tablet is 90.0-110.0%, A rapid disintegration of the tablet is observed following dissolution in the range of 20 to 40 sec at 25° C./60% RH.

The disintegration property of the dispersible tablet is likely due to its disintegrant component, for example, Sodium croscarmellose that promotes the breakup or disintegration of the tablet when placed in an aqueous environment and supports a fast dissolution profile. In addition, the wetting agent, for example, Poloxamer 188, facilitates the water uptake during the disintegration and assists the drug dissolution. Furthermore, the carrier agent selected with a large surface area, for example Calcium silicate, was also identified as a potential benefit for the disintegration of the tablet.

TABLE 28

Dispersible tablet of 50 mg

| Storage conditions | Storage Time (months) | Tablet appearance | Water content (% w/w) | (3Z, 5S) Content (% intial value) | Disintegr. Time (sec) | % Dissolved after 60 min |
|---|---|---|---|---|---|---|
| Initial | 0 | White capsule shaped | 4.5 | 102.9 | 42 | 101 |
| 5 °C. | 1 | White capsule shaped | 4.7 | 102.4 | 19 | 100 |
|  | 2 | White capsule shaped | 4.6 | 102.2 | 17 | 100 |
|  | 6 | White capsule shaped | 4.8 | 103.3 | 26 | 99 |
| 25 °C./60% RH | 1 | White capsule shaped | 4.6 | 102.2 | 16 | 97 |
|  | 2 | White capsule shaped | 4.6 | 103.8 | 22 | 97 |
|  | 6 | Off-white capsule shaped | 4.7 | 105.7 | 28 | 99 |
| 40 °C./75% RH | 1 | White capsule shaped | np | np | np | np |
|  | 2 | Off white capsule shaped | 4.5 | 99.9 | 50 | 95 |
|  | 6 | Yellowish capsule shaped* | 4.6 | 102.1 | 113 | 94 | np = not performed

TABLE 29

Dispersible tablet of 200 mg

| Storage conditions | Storage Time (months) | Tablet appearance | Water content (% w/w) | (3Z, 5S) Content (% intial value) | Disintegr. Time (sec) | % Dissolved after 60 min |
|---|---|---|---|---|---|---|
| Initial | 0 | White capsule shaped | 4.5 | 98.1 | 102 | 93 |
| 5 °C. | 1 | White capsule shaped | 4.0 | 97.7 | 26 | 99 |
|  | 2 | White capsule shaped | 4.3 | 97.7 | 26 | 96 |
|  | 6 | White capsule shaped | 4.1 | 99.7 | 28 | 99 |
| 25 °C./60% RH | 1 | White capsule shaped | 4.0 | 98.0 | 26 | 96 |
|  | 2 | White capsule shaped | 4.2 | 98.9 | 28 | 100 |
|  | 6 | Off-white capsule shaped | 4.1 | 99.5 | 40 | 98 |
| 40 °C./75% RH | 1 | White capsule shaped | np | np | np | np |
|  | 2 | Off white capsule shaped | 4.2 | 96.6 | 107 | 98 |
|  | 6 | Yellowish capsule shaped* | 4.1 | 98.3 | 170 | 96 | np = not performed

TABLE 30

Dissolution profile of 200 mg dispersible tablet and content of (3Z, 5S) at 15, 30, 45, 60 and 120 min.

| Storage Condition | Time (Months) | 15 min (3Z, 5S) Content % | 30 min (3Z, 5S) Content % | 45 min (3Z, 5S) Content % | 60 min (3Z, 5S) Content % | 120 min (3Z, 5S) Content % |
|---|---|---|---|---|---|---|
| Initial | 0 | 89 | 94 | 96 | 97 | 99 |
| 5 °C./AmbH | 1 | 91 | 95 | 96 | 97 | 99 |
|  | 3 | 92 | 95 | 97 | 97 | 99 |
|  | 6 | 95 | 98 | 98 | 100 | 101 |
| 25 °C./60% RH | 1 | 93 | 95 | 96 | 97 | 98 |
|  | 3 | 94 | 97 | 98 | 98 | 100 |
|  | 6 | 97 | 99 | 100 | 100 | 102 |
| 40 °C./75% RH | 1 | 96 | 98 | 99 | 99 | 100 |
|  | 3 | 95 | 97 | 97 | 98 | 99 |
|  | 6 | 95 | 97 | 98 | 98 | 99 |

A rapid dissolution profile of the tablet is observed for the different storage conditions. In particular, at 25° C./60% RH, the content of (3Z,5S) measured at 15 min is between 90 to 100% of the initial value.

The invention claimed is:

1. A dispersible tablet comprising a substantially pure form of (3Z,5S)-5-(hydroxymethyl)-1-[(2'-methyl-1,1'-biphenyl-4-yl)carbonyl]pyrrolidin-3-one-O-methyloxime, and one or more pharmaceutically acceptable excipients.

2. The dispersible tablet according to claim 1, wherein said dispersible tablet is in a unit dose.

3. The dispersible tablet according to claim 1, wherein the purity of said (3Z,5S)-5-(hydroxymethyl)-1-[(2'-methyl-1,1'-biphenyl-4-yl)carbonyl]pyrrolidin-3-one-O-methyloxime is from about 85% to about 99.9%.

* * * * *